United States Patent
Briskin

(10) Patent No.: US 6,423,514 B1
(45) Date of Patent: Jul. 23, 2002

(54) MAMMALIAN HYALURONAN SYNTHASES, NUCLEIC ACIDS AND USES THEREOF

(75) Inventor: Michael J. Briskin, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 555 days.

(21) Appl. No.: 08/635,552

(22) Filed: Apr. 22, 1996

(51) Int. Cl.$^7$ .......................... C12N 9/00; C12N 15/11; C12N 15/63; C12P 19/26
(52) U.S. Cl. ...................... 435/84; 435/183; 435/252.3; 435/320.1; 435/325; 435/101; 536/23.2
(58) Field of Search .............................. 435/183, 320.1, 435/240.1, 252.3, 325, 84, 101; 536/23.2

(56) References Cited

FOREIGN PATENT DOCUMENTS

| | | |
|---|---|---|
| WO | WO 94/00463 | 1/1994 |
| WO | WO 97/38113 | 10/1997 |

OTHER PUBLICATIONS

Itano (1996) Human fetal brain mRNA for hyaluronan synthase, complete cds., Genbank Acc. No. (GBN): D84424, submitted Apr. 16, 1996, STN Online, CAS Registry No. 178197–91–6, Chemical Abrtracts, Columbus OH.*
Watanabe et al. (1996) Human Has2 mRNA, complete cds., Genbank Acc. No. (GBN): U54804, submitted Apr. 11, 1996, STN Online, CAS Registry No. 179788–75–1, Chemical Abstracts, Columbus, OH.*
Rudinger (1976) Characteristics of the amino acids as components of a peptide hormone sequence. In: Peptide Hormones, Ed. J. A. Parsons, University Park Press, Baltimore, MD, pp. 1–7, Jun. 1976.*
Itano, N. and Kimata, K., "Expression Cloning and Molecular Characterization of HAS Protein, a Eukaryotic Hyaluronan Synthase", *J. of Biol. Chemistry*, 271(17):9875–9878 (Apr. 1996).
Prehm, P., "Identification and regulation of the eukaryotic hyaluronate synthase", *The Biology of Hyaluronan*, (Ciba Foundation Symposium 143), pp. 21–40 (1989).
DeAngelis, P.L., et al., "The *Streptococcus pyogenes* Hyaluronan Synthase: Sequence Comparison and Conservation Among Various Group A Strains", *Biochemical and Biophysical Res. Communications*, 199(1):1–10 (1994).
Rosa, F., et al., "Accumulation and Decay of DG42 Gene Products follow a Gradient Pattern during Xenopus Embryogenesis", *Developmental Biology*, 129:114–123 (1988).
Klewes, L., et al., "The hyaluronate synthase from a eukaryotic cell line", *Biochem. J.*, 290:791–795 (1993, printed in Great Britain).
DeAngelis, P.L., et al., "Molecular Cloning, Identification, and Sequence of the Hyaluronan Synthase Gene from Group A *Streptococcus pyogenes*", *The J. of Biol. Chem.*, 268(26):19181–19184 (1993).

Mian, N., "Characterization of a high–$M_r$ plasma–membrane–bound protein and assessment of its role as a constituent of hyaluronate synthase complex", *Biochem. J.*, 237:343–357 (1986).
Ng, K.F. and Schwartz, N.B., "Solubilization and Partial Purification of Hyaluronate Synthetase from Oligodendroglioma Cells", *The J. of Biol. Chem.*, 264(20):11776–11783 (1989).
Dougherty, B.A. and van de Rijn, I., "Molecular Characterization of hasA from an Operon Required for Hyaluronic Acid Synthesis in Group A Streptococci", *The J. of Biol. Chem.*, 269(1):169–175 (1994).
Semino, C.E. and Robbins, P.W., "Synthesis of "Nod"–like chitin oligosaccharides by the Xenopus developmental protein DG42", *Proc. Natl. Acad. Sci. USA*, 92:3498–3501 (1995).
Klewes, L. and Prehm, P., "Intracellular Signal Transduction for Serum Activation of the Hyaluronan Synthase in Eukaryotic Cell Lines", *J. of Cell. Physiology*, 160:539–544 (1994).
Heldin, P., et al., "Characterization of the molecular mechanism involved in the activation of hyaluronan synthetase by platelet–derived growth factor in human mesothelial cells", *Biochem. J.*, 283:165–170 (1992).
O'Regan, M., et al., "Molecular mechanisms and genetics of hyaluronan biosynthesis", *Int. J. Biol. Macromol.*, 16(6)283–286 (1994).
Laurent, T.C. and Fraser, J.R.E., "Hyaluronan", *FASEB J.*, 6:2397–2404 (1992).
Dougherty, B.A. and van de Rijn, I., "Molecular Characterization of hasB from an Operon Required for Hyaluronic Acid Synthesis in Group A Streptococci", *The J. of Biol. Chem.*, 268(10):7118–7124 (1993).

(List continued on next page.)

Primary Examiner—Rebecca E. Prouty
Assistant Examiner—Richard Hutson
(74) Attorney, Agent, or Firm—Hamilton, Brook, Smith & Reynolds, P.C.

(57) ABSTRACT

The present invention relates to an isolated or recombinant nucleic acid which encodes a mammalian hyaluronan synthase (e.g. human). The present invention also relates to a host cell comprising the nucleic acid encoding mammalian hyaluronan synthase. The present invention also relates to a method for producing a mammalian hyaluronan synthase comprising introducing into a host cell a nucleic acid construct comprising a nucleic acid which encodes a mammalian hyaluronan synthase, whereby a recombinant host cell is produced having said coding sequence operably linked to at least one expression control sequence; and maintaining the host cells produced in a suitable medium under conditions whereby the nucleic acid is expressed. The present invention also relates to an antibody or functional portion thereof which binds mammalian hyaluronan synthase. The present invention also relates to a method of detecting mammalian hyaluronan synthase in a sample comprising contacting a sample with an antibody which binds hyaluronan synthase under conditions suitable for specific binding of said antibody to the mammalian hyaluronan synthase; and detecting antibody-mammalian hyaluronan synthase. The invention further relates to a method of using hyaluronan synthase to make hyaluronan.

14 Claims, 7 Drawing Sheets

OTHER PUBLICATIONS

Knudson, C.B. and Knudson, W., "Hyaluronan–binding proteins in development, tissue homeostasis, and disease", *FASEB J.*, 7,: 1233–1241 (1993).

Crater, D.L. and van de Rijn, I., "Hyaluronic Acid Synthesis Operon (has) Expression in Group A Streptococci", *J. of Biol. Chem.*, 270(31):18452–18458 (1995).

Prehm, P., "Synthesis of hyaluronate in differentiated teratocarcinoma cells", *Biochem. J.*, 211:181–189 (1983).

Philipson, L.H. and Schwartz, N.B., "Subcellular Localization of Hyaluronate Synthetase in Oligodendroglioma Cells", *J. of Biol. Chem.*, 259(8):5017–5023 (1984).

Asplund, T., et al., "Human Mesothelioma Cells Produce Factors That Stimulate the Production of Hyaluronan by Mesothelial Cells and Fibroblasts", *Cancer Research*, 53:388–392 (1993).

Itano, N. and Kimata, K., "Molecular Cloning of Human Hyaluronan Synthase", *Biochemical and Biophysical Res. Communications*, 222:816–820 (1996).

Shyjan, A.M. et al., "Functional cloning of the cDNA for a human hyaluronan synthase", *J. Biol. Chem.*, 271(38):23395–23399 (1996).

Watanabe, K. et al., "Molecular identification of a putative human hyaluronan synthase", *J. Biol. Chem.*, 271 (38): 22945–22948 (1996).

Spicer, A.P. et al., "Molecular cloning and characterization of a cDNA encoding the third putative mammalian hyaluronan synthase", *J. Biol. Chem.*, 272(14):8957–8961 (1997).

Fülop, C. et al., "Coding sequence of a hyaluronan synthase homologue expressed during expansion of the mouse cumulus–oocyte complex", *Arch. Biochem. Biophys.*, 337(2):261–266 (1997).

Spicer, A.P. et al., "Molecular cloning and characterization of a putative mouse hyaluronan synthase", *J. Biol. Chem.*, 271(38):23400–23406 (1996).

* cited by examiner

```
CGGAGAGAAGAGAGAGCCCGGCCAGACCCACTGCGATGAGACAGCAGGACGCGCCCAAGCCCACTCCTGCAGCCCGCCGC  80
                                        M  R  Q  Q  D  A  P  K  P  T  P  A  A  R  R
TGCTCCGGCCTGGCCCGGAGGGTGCTGACCATCGCCTTCGCCCTGCTCATCCTGGGCCTCATGACCTGGGCCTACGCCGC  160
 C  S  G  L  A  R  R  V  L  T  I  A  F  A  L  L  I  L  G  L  M  T  W  A  Y  A  A
CGGGGTGCCGCTGGCCTCCGATCGCTACGGGCTCCTGGCCTTCGGCCTCTACGGGGCCTTCCTTTCAGCGCACCTGGTGG  240
  G  V  P  L  A  S  D  R  Y  G  L  L  A  F  G  L  Y  G  A  F  L  S  A  H  L  V
CGCAGAGCCTCTTCGCGTACCTGGAGCACCGGCGGGTGGCGGCGGCGGCGCGGGGGCCGCTGGATGCAGCCACCGCGCGC  320
  A  Q  S  L  F  A  Y  L  E  H  R  R  V  A  A  A  A  R  G  P  L  D  A  A  T  A  R
AGTGTGGCGCTGACCATCTCCGCCTACCAGGAGGACCCCGCGTACCTGCGCCAGTGCCTGGCGTCCGCCCGCGCCCTGCT  400
  S  V  A  L  T  I  S  A  Y  Q  E  D  P  A  Y  L  R  Q  C  L  A  S  A  R  A  L  L
GTACCCGCGCGCGGCTGCGCGTCCTCATGGTGGTGGATGGCAACCGCGCCGAGGACCTCTACATGGTCGACATGTTCC  480
  Y  P  R  A  R  L  R  V  L  M  V  V  D  G  N  R  A  E  D  L  Y  M  V  D  M  F
GCGAGGTCTTCGCTGACGAGGACCCCGCCACGTACGTGTGGGACGGCAACTACCACCAGCCCTGGGAACCCGCGGCGGCG  560
  R  E  V  F  A  D  E  D  P  A  T  Y  V  W  D  G  N  Y  H  Q  P  W  E  P  A  A  A
GGCGCGGTGGGCGCCGGAGCCTATCGGGAGGTGGAGGCGGAGGATCCTGGGCGGCTGGCAGTGGAGGCGCTGGTGAGGAC  640
  G  A  V  G  A  G  A  Y  R  E  V  E  A  E  D  P  G  R  L  A  V  E  A  L  V  R  T
TCGCAGGTGCGTGTGCGTGGCGCAGCGCTGGGCGGCAAGCGCGAGGTCATGTACACAGCCTTCAAGGCGCTCGGAGATT  720
  R  R  C  V  C  V  A  Q  R  W  G  G  K  R  E  V  M  Y  T  A  F  K  A  L  G  D
CGGTGGACTACGTGCAGGTCTGTGACTCGGACACAAGGTTGGACCCCATGGCACTGCTGGAGCTCGTGCGGGTACTGGAC  800
  S  V  D  Y  V  Q  V  C  D  S  D  T  R  L  D  P  M  A  L  L  E  L  V  R  V  L  D
GAGGACCCCCGGGTAGGGGCTGTTGGTGGGGACGTGCGGATCCTTAACCCTCTGGACTCCTGGGTCAGCTTCCTAAGCAG  880
  E  D  P  R  V  G  A  V  G  G  D  V  R  I  L  N  P  L  D  S  W  V  S  F  L  S  S
CCTGCGATACTGGGTAGCCTTCAATGTGGAGCGGGCTTGTCAGAGCTACTTCCACTGTGTATCCTGCATCAGCGGTCCTC  960
  L  R  Y  W  V  A  F  N  V  E  R  A  C  Q  S  Y  F  H  C  V  S  C  I  S  G  P
TAGGCCTATATAGGAATAACCTCTTGCAGCAGTTTCTTGAGGCCTGGTACAACCAGAAGTTCCTGGGTACCCACTGTACT  1040
  L  G  L  Y  R  N  N  L  L  Q  Q  F  L  E  A  W  Y  N  Q  K  F  L  G  T  H  C  T
TTTGGGGATGACCGGCACCTCACCAACCGCATGCTCAGCATGGGTTATGCTACCAAGTACACCTCCAGGTCCCGCTGCTA  1120
  F  G  D  D  R  H  L  T  N  R  M  L  S  M  G  Y  A  T  K  Y  T  S  R  S  R  C  Y
CTCAGAGACGCCCTCGTCCTTCCTGCGGTGGCTGAGCCAGCAGACACGCTGGTCCAAGTCGTACTTCCGTGAGTGGCTGT  1200
  S  E  T  P  S  S  F  L  R  W  L  Q  Q  T  R  W  S  K  S  Y  F  R  E  W  L
ACAACGCGCTCTGGTGGCACCGGCACCATGCGTGGATGACCTACGAGGCGGTGGTCTCCGGCCTGTTCCCCTTCTTCGTG  1280
  Y  N  A  L  W  W  H  R  H  H  A  W  M  T  Y  E  A  V  V  S  G  L  F  P  F  F  V
GCGGCCACTGTGCTGCGTCTGTTCTACGCGGGCCGCCCTTGGGCGCTGCTGTGGGTGCTGCTGTGCGTGCAGGGCGTGGC  1360
  A  A  T  V  L  R  L  F  Y  A  G  R  P  W  A  L  L  W  V  L  L  C  V  Q  G  V  A
ACTGGCCAAGGCGGCCTTCGCGGCCTGGCTGCGGGGCTGCCTGCGCATGGTGCTTCTGTCGCTCTACGCGCCCCTCTACA  1440
  L  A  K  A  A  F  A  A  W  L  R  G  C  L  R  M  V  L  L  S  L  Y  A  P  L  Y
TGTGTGGCCTCCTGCCTGCCAAGTTCCTGGCGCTAGTCACCATGAACCAGAGTGGCTGGGGCACCTCGGGCCGGCGGAAG  1520
  M  C  G  L  L  P  A  K  F  L  A  L  V  T  M  N  Q  S  G  W  G  T  S  G  R  R  K
CTGGCCGCTAACTACGTCCCTCTGCTGCCCTGGCGCTCTGGGCGCTGCTGCTGCTTGGGGGCCTGGTCCGCAGCGTAGC  1600
  L  A  A  N  Y  V  P  L  L  P  L  A  W  A  L  L  L  L  G  G  L  V  R  S  V  A
ACACGAGGCCAGGGCCGACTGGAGCGGCCCTTCCCGCGCAGCCGAGGCCTACCACTTGGCCGCGGGGCCGGCGCCTACG  1680
  H  E  A  R  A  D  W  S  G  P  S  R  A  A  E  A  Y  H  L  A  A  G  A  G  A  Y
TGGGCTACTGGGTGGCCATGTTGACGCTGTACTGGGTGGGCGTGCGGAGGCTTTGCCGGCGGCGGACCGGGGCTACCGC  1760
  V  G  Y  W  V  A  M  L  T  L  Y  W  V  G  V  R  R  L  C  R  R  R  T  G  G  Y  R
GTCCAGGTGTGAGTCCAGCCACGCGGATGCCGCCTCAAGGGTCTTCAGGGGAGGCAGAGGAGAGCTGCTGGGCCCGAG  1840
  V  Q  V
CCACGAACTTGCTGGGTGGTTCTCTGGGCCTCAGTTTCCCTCCTCTGCCAAACGAGGGGGTCAGCCCAAGATTCTTCAGT  1920
CTGGACTATATTGGGACTGGGACTTCTGGGTCTCCAGGGAGGGTATTTATTGGTCAGGATGTGGGATTTGAGGAGTGGAG  2000
GGGAAAGGGTCCTGCTTTCTCCTCGTTCTTATTTAATCTCCATTTCTACTGTGTGATCAGGATGTAATAAAGAATTTTAT  2080
TTATTTTCAAAAAAAAAAAAAAAAAAAAAAAAAAAAA  2116
```

FIG. 2

```
                  10                  20                  30
 1  M R Q Q D A P K - - - - - - - - P T P A A R R C S G L A R R V   HAS
 1  M - - - - - - - - - - - - - - - - - - - - - - - - - - - - - -   hasA
 1  M K E K A A E T M E I P E G I P K D L E P K H P T L - W R I   DG42

TM1  40                  50                  60
24  L T I A F A L L I L G L M T W A Y A A G V P L A S D R Y G L   HAS
 2  - - Y L F G T S - - - - - - - - - - - - - - - - - - - - - -   hasA
30  I Y Y S F G V V L A T I T A Y V A E F Q V L K H E A I L   DG42

70                  80                  90
54  L A F G L Y G A F L S A H L V Q S L F A Y L E H R R V A A   HAS
 8  - T V G I Y G V I L I T Y L V I K L G L S F L - - - - - Y E   hasA
60  F S L G L Y G L A M L L H L M M Q S L F A F L E I R R V N -   DG42

100                 110                 120
84  A A R G P L D A A T A R S V A L T I S A Y Q E D P A Y L R Q   HAS
32  P F K G N - - - P H D Y K V A A V I P S Y N E D A E S L L E   hasA
89  - - K S E L P C S F K K T V A L T I A G Y Q E N P E Y L I K   DG42

130                 140                 150
114 C L A S A R A L L Y P R A R L R V L M V V D G N R A E D L Y   HAS
59  T L K S V L A Q T Y P L S - - E I Y I V D D G S S N T D A -   hasA
117 C L E S C K Y V K Y P K D K L K I I L V I D G N T E D D A Y   DG42

160                 170                 180
144 M V D M F R E V F A D E D P A T Y V W D G N Y H Q P W E P A   HAS
86  - I Q L I E E - Y V N R E V D I C - - - - - - - - - - - - -   hasA
147 M M E M F K D V F H G E D V G T Y V W K G N Y H T V K K P E   DG42

190                 200                 210
174 A A G A V G A G A Y R E V E A E D P G R L A V E A L V R T R   HAS
101 - - - - - - - - - - - - - - - R N V I V H R S L V N K -   hasA
177 E T N K G S C P E V S K P L N E D E G I N M V E L V R N K   DG42

220                 230                 240
204 R C V C V A Q R W G G K R E V M Y T A F K A L G D S V D Y V   HAS
113 - - - - - - - - - G K R H A Q A W A F E R S D A D V - F L   hasA
207 R C V C I M Q Q W G G K R E V M Y T A F Q A I G T S V D Y V   DG42

250                 260                 270
234 Q V C D S D T R L D P M A L L E L V R V L D E D P R V G A V   HAS
132 T V - D S D T Y I Y P N A L E E L L K S F N D E T V Y A A T   hasA
237 Q V C D S D T K L D E L A T V E M V K V L E S N D M Y G A V   DG42

280                 290                 300
264 G G D V R I L N P L D S W V S F L S S L R Y W V A F N V E R   HAS
161 G - H L N A R N R Q T N L L T R L T D I R Y D N A F G V E R   hasA
267 G G D V R I L N P Y D S F I S F M S S L R Y W M A F N V E R   DG42
```

FIG. 3A

```
                    310              320              330
294  A C Q S Y F H C V S C I S G P L G L Y R N N L Q Q F L E A   HAS
190  A A Q S L T G N I L V C S G P L S I Y R R E V I I P N L E R  hasA
297  A C Q S Y F D C V S C I S G P L G M Y R N N I L Q V F L E A  DG42

340              350              360
324  W Y N Q K F L G T H C T F G D D R H L T N R M L S M G Y A T  HAS
220  Y K N Q T F L G L P V S I G D D R C L T N Y A I D L G - R T  hasA
327  W Y R Q K F L G T Y C T L G D D R H L T N R V L S M G Y R T  DG42

370              380              390
354  K Y T S R S R C Y S E T P S S F L R W L S Q Q T R W S K S Y  HAS
249  V Y Q S T A R C D T D V P F Q L K S Y L K Q Q N R W N K S F  hasA
357  K Y T H K S R A F S E T P S L Y L R W L N Q Q T R W T K S Y  DG42

400              410              420
384  F R E W L Y N A L W W H R H H A - - - W M T Y E A V V S G L  HAS
279  F R E S I I S V K K I L S N P I V A L W T I F E V V - - - M  hasA
387  F R E W L Y N A Q W W H K H H I - - - W M T Y E S V V S F I  DG42

430              440   TM2        450
411  F P F F V A A T V L R L F Y A G R P W A L L W V L - - L C V  HAS
306  F M M L I V A I G N L L F N Q A I Q L D L I K L F A F L S I  hasA
414  F P F F I T A T V I R L I Y A G T I W N V V W L L - - L C I  DG42

460              470              480
439  Q - G V A L A K A A - F A A W L R G C L R M V L L S L Y A P  HAS
336  I F I V A L C R N V H Y M V K H P A S F - - L L S P L Y G I  hasA
442  Q - I M S L F K S I - Y A C W L R G N F I M L L M S L Y S M  DG42

490              500              510
467  L Y M C G L L P A K F L A L V T M N Q S G W G T S G R R K L  HAS
364  L H L F V L Q P L K L Y S L C T I K N T E W G T - - R K K V  hasA
470  L Y M T G L L P S K Y F A L L T L N K T G W G T   G R K K I  DG42

520    TM3   530              540
497  A A N Y V P L L P L A L W A L L L L G G L V R S V A H E A R  HAS
392  T - - - - - - - - - - - - - - - - - - - - - - - - - - - -   hasA
500  V G N Y M P I L P L S I W A A V L C G G V G Y S I Y M D C Q  DG42

550              560   TM4         570
527  A D W S G P S R A A E A Y H L A A G A G A Y V G Y W V A M L  HAS
393  - - - - - - - - - - - I F K                                 hasA
530  N D W S T P E K Q K E M Y H L Y G C V G Y V M Y W V I M A   DG42

580              590
557  T L Y W V G V R R L C R R R T G G Y R V Q - - - - - - - V   HAS
395                                                              hasA
560  V M Y W V W V K R C C R K R S Q T V T L V H D I P D M C V   DG42
```

FIG. 3B

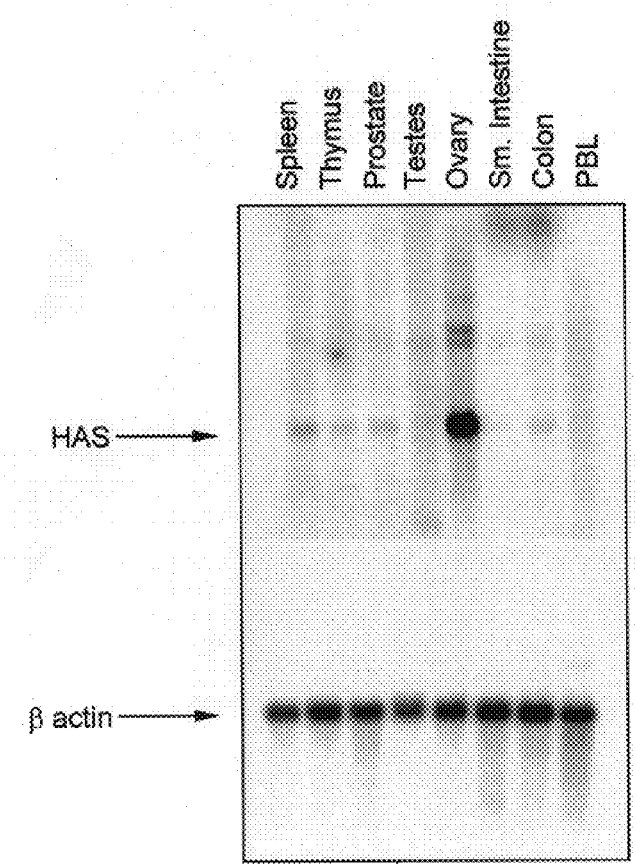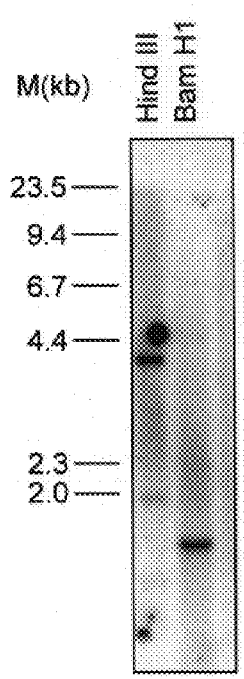

MAMMALIAN HYALURONAN SYNTHASES, NUCLEIC ACIDS AND USES THEREOF

BACKGROUND

Hyaluronan is a constituent of the extracellular matrix of connective tissue, and is actively synthesized during wound healing and tissue repair to provide a framework for ingrowth of blood vessels and fibroblasts. Changes in the serum concentration of hyaluronan are associated with inflammatory and degenerative arthropathies such as rheumatoid arthritis. In addition, hyaluronan has been implicated as an important substrate for migration of adhesion of leukocytes during inflammation.

Hyaluronan (hyaluronic acid, HA) is a high molecular mass polysaccharide that has ubiquitous distribution in the extracellular matrix, with highest concentrations in soft connective tissue. It is a linear polysaccharide comprising alternating glucuronic acid and N-acetylglucosamine residues linked by β-1-3 and β-1-4 glycosidic bonds (Laurent, T. C. et al. (1986), "The properties and turnover of hyaluronan." Functions of proteoglycans (*Symposium, C. F., Ed.* 124, Chichester, England). By interacting with other matrix molecules, such as chondroitin sulfate proteoglycans, hyaluronan provides stability and elasticity to the extracellular matrix. Hyaluronan has several physiochemical and biological functions such as space filling, lubrication, and providing a hydrated matrix through which cells can migrate (Toole, B. P. et al., *Hyaluronate-cell interactions. The role of the extracellular matrix in development,* (Trelstad, R. L., Ed., Alan R. Liss, New York (1984); Laurent, T. C. et al., *Faseb J.* 6:2397–2404 (1992)). Interaction of hyaluronan with the leukocyte cell surface receptor CD44 has been shown to contribute to organ specific leukocyte homing and migration (Jalkanen, S. T. et al., *J. Cell. Biol.,* 105:893–990 (1987); Aruffo, A., et al., *Cell* 61:1303–1313 (1990); Culty, M. et al., *J. Cell. Biol.,* 111:2765–2774 (1990); Miyake, K. et al., *J. Exp. Med.* 172:69–75 (1990); Sherman, L. et al., *Current opinions in Cell Biology,* 6:726–733 (1994)). Hyaluronan synthesis has been suggested to be required for cellular proliferation (Brecht, M. et al., *Biochem. J.* 239:445–450 (1986); Hronowski, L. and Anastassiades, T. P., *J. Biol. Chem.* 255:9210–9217 (1980); Matuoka, K. et al., *J. Cell Biol.* 104:1105–1115 (1987); Mian, N., *Biochem. J.* 237:333–342 (1986); Tomida, M. et al., *J. Cell Physiol.* 86:121–130 (1975)), and over-expression of receptors for hyaluronan, including a receptor for hyaluronan mediated motility (RHAMM) and CD44, correlates with increased levels of tumor metastasis (Gunthert, U., *Curr. Topics Microbiol. Immunol.* 184:47–63 (1993); Hall, C. L. et al., *Cell* 82:19–28 (1995); Turley, E. A., *Cancer and Metastasis Reviews* 11:1233–1241 (1992)). Purified preparations of hyaluronan exhibit unique viscoelastic properties, and as a consequence of these characteristics have been used in viscoelastic surgery and viscosupplementation (Balazs, E. A., and Denninger, J. L., Clinical uses of hyaluronan, *The biology of hyaluronan, Ciba foundation symposium,* Wiley, Chichester, England (1989)). Hyaluronan is synthesized mainly by mesenchymal cells and the accumulation of HA is an early event in tissue repair. The serum level of hyaluronan is elevated in inflammatory settings such as rheumatoid arthritis, osteoarthritis, liver cirrhosis, Werner's syndrome, renal failure and psoriasis (Laurent, T. C. et al., *Faseb J.* 6:2397–2404 (1992); Laurent, T. C. *Annals of Medicine* 28:in press (1996)).

Hyaluronan is synthesized by a membrane bound synthase; monosaccharide and disaccharide residues are added to the reducing end of the polysaccharide as it protrudes through the plasma membrane (Prehm, P., *Biochem. J.* 211:181–189 (1983); Prehm, P., *Biochem. J.* 220:597–600 (1984)). Regulation of hyaluronan biosynthesis has been studied in several tissue culture systems. Factors involved in tissue growth and repair such as different isoforms of platelet derived growth factor (PDGF-AA, PDGF-BB), epidermal growth factor (EGF), basic fibroblast growth factor (bFGF), and transforming growth factor β(TGF-β), all exhibit stimulatory activity on hyaluronan biosynthesis (Heldin, P. et al., *Biochem. J.* 258, 919–922 (1992)).

A cDNA encoding a bacterial hyaluronan synthase has been cloned from *Streptococcus pyogenes* (hasA) (DeAngelis, J. P. et al., *J. Biol. Chem.* 268, 19181–19184 (1993)). Other related genes with N-acetylglucosaminyl transferase activity have been isolated from the nitrogen fixing bacteria Rhizobium (nodC) and chitin synthases (Chs) from Saccharomyces (DeAngelis, P. L. et al., *Biochem. Biophys. Res. Comm.* 199:1–10 (1994)). A putative vertebrate homolog, (DG42), was cloned from *Xenopus laevis* and has also been speculated to be a glycosaminoglycan synthetase (Rosa, F. et al., *Develop. Biol.* 129:114–123 (1988)). To date, however, a mammalian hyaluronan synthase gene has not been identified.

SUMMARY OF THE INVENTION

The present invention relates to isolated and/or recombinant nucleic acids which encode a mammalian hyaluronan synthase (e.g., human). In one embodiment, the nucleic acid of the present invention comprises SEQ ID NO:1. In another embodiment, the invention relates to a nucleic acid wherein said nucleic acid hybridizes under stringent conditions with a second nucleic acid having a nucleotide sequence of SEQ ID NO: 1.

The present invention also relates to a host cell comprising a nucleic acid encoding mammalian hyaluronan synthase. In a particular embodiment, the host cell comprises nucleic acid encoding mammalian hyaluronan synthase which is operably linked to an expression control sequence, whereby mammalian hyaluronan synthase is expressed when the host cell is maintained under conditions suitable for expression.

The present invention also relates to a method for producing a mammalian hyaluronan synthase comprising introducing into a host cell a nucleic acid construct comprising a nucleic acid which encodes a mammalian hyaluronan synthase, whereby a recombinant host cell is produced having said coding sequence operably linked to an (i.e., at least one) expression control sequence; and maintaining the host cells produced in a suitable medium under conditions whereby the nucleic acid is expressed.

The present invention also relates to an antibody or functional portion thereof (e.g., an antigen binding portion such as an Fv, Fab, Fab', or F(ab')$_2$ fragment) which binds mammalian hyaluronan synthase.

The present invention also relates to a method of detecting mammalian hyaluronan synthase in a sample comprising contacting a sample with an antibody which binds hyaluronan synthase under conditions suitable for specific binding of said antibody to the mammalian hyaluronan synthase; and detecting antibody-mammalian hyaluronan synthase.

The invention further relates to a method of using hyaluronan synthase to make hyaluronan.

BRIEF DESCRIPTION OF THE FIGURES

FIG. 2 is an illustration of the nucleotide sequence (SEQ ID NO:1) and deduced protein sequence (SEQ ID NO:2) determined from human hyaluronan synthase cDNA clone 30C; cysteine residues are circled and a conserved motif, $B(X_7)B$, believed to be important for binding hyaluronan is lightly outlined; consensus phosphorylation sequences for protein kinase C (RHLT, KYT and RWLS) and cAMP dependent protein kinases (RWS) are outlined in bold; also shown with a bold underline at position 2066 is a consensus polyadenylation signal, AATAAA. (Standard single letter amino acid codes are used.)

FIGS. 3A–3B show an amino acid alignment of the human hyaluronan synthase protein sequence (SEQ ID NO:2) with the DG42 sequence from Xenopus laevis (SEQ ID NO:3) and hasA sequence of Streptococcus pyogenes (SEQ ID NO:4) prepared using the DNAStar program and the Clustal method with default parameters for gap penalties.

FIG. 4A is a Northern blot probed with the full length insert of the human hyaluronan synthase cDNA clone 30C; the blot was subsequently stripped and reprobed with a β-actin cDNA as a control.

FIG. 4B is a Southern blot initially hybridized with full-length human hyaluronan synthase cDNA, washed at 50° C., and exposed overnight; a considerable amount of background was seen although specific bands could be detected; subsequently the blot was stripped and probed with a 450 bp Sac II fragment encompassing the 3' end of the cDNA; this probe gave a similar pattern with less background (likely due to a lower GC content).

DETAILED DESCRIPTION OF THE INVENTION

Proteins and Peptides

Figure 1A:
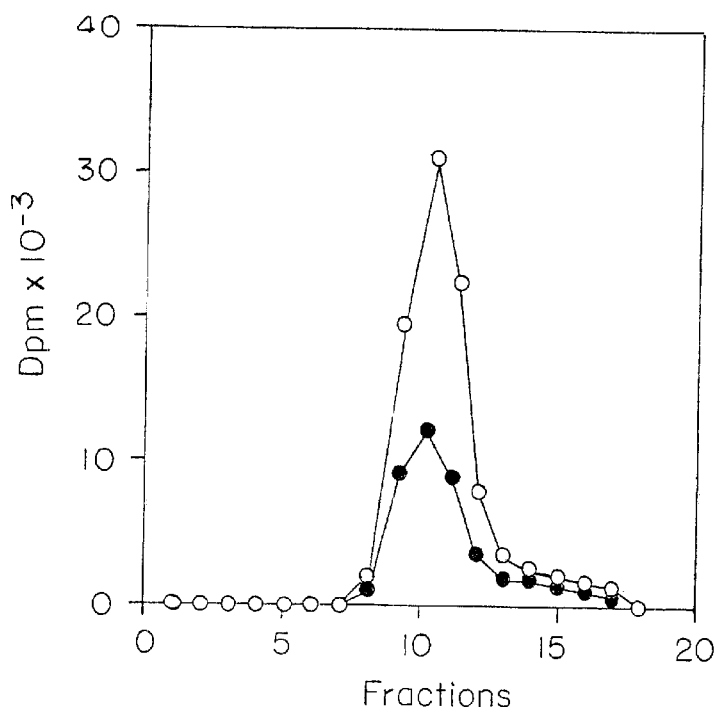
FIG. 1A is a graph illustrating that CHO cells tranfected with human hyaluronan synthase cDNA synthesize hyaluronic acid; media and cell lysates were combined and then incubated overnight in the absence (o---o) or presence (●---●) of 10U Streptomyces hyaluronidase/ml and subjected to chromatography on Sephadex G-50 columns; Streptomyces hyaluronidase-sensitive radioactivity represents synthesized hyaluronan.

The present invention relates to isolated and/or recombinant (including, e.g., essentially pure) proteins or polypeptides designated mammalian hyaluronan synthase and variants of mammalian hyaluronan synthase. In a preferred embodiment, the isolated and/or recombinant proteins of the present invention have at least one property, activity or function characteristic of a mammalian hyaluronan synthase (as defined herein), such as activity in the synthesis of hyaluronan and/or ability to confer of cell adhesion by the lymphocyte receptor CD44 (i.e., human CD44 or a mammalian homolog thereof).

Proteins or polypeptides referred to herein as "isolated" are proteins or polypeptides purified to a state beyond that in which they exist in mammalian cells. "Isolated" proteins or polypeptides include proteins or polypeptides obtained by methods described herein, similar methods or other suitable methods, including essentially pure proteins or polypeptides proteins or polypeptides produced by chemical synthesis (e.g., synthetic peptides), or by combinations of biological and chemical methods, and recombinant proteins or polypeptides which are isolated. The proteins can be obtained in an isolated state of at least about 50% by weight, preferably at least about 75% by weight, and more preferably, in essentially pure form. Proteins or polypeptides referred to herein as "recombinant" are proteins or polypeptides produced by the expression of recombinant nucleic acids.

As used herein "mammalian hyaluronan synthase" refers to naturally occurring or endogenous mammalian hyaluronan synthase proteins, to proteins having an amino acid sequence which is the same as that of a naturally occurring or endogenous corresponding mammalian hyaluronan synthase (e.g., recombinant proteins), and to functional variants of each of the foregoing (e.g., functional fragments and/or mutants produced via mutagenesis and/or recombinant techniques). Accordingly, as defined herein, the term includes mature mammalian hyaluronan synthase, glycosylated or unglycosylated mammalian hyaluronan synthase proteins, polymorphic or allelic variants, and other isoforms of mammalian hyaluronan synthase (e.g., produced by alternative splicing or other cellular processes), and functional fragments.

Naturally occurring or endogenous mammalian hyaluronan synthase proteins include wild type proteins such as mature mammalian hyaluronan synthase, polymorphic or allelic variants and other isoforms which occur naturally in mammals (e.g., primate, preferably human, murine, bovine). Such proteins can be recovered from a source which naturally produces mammalian hyaluronan synthase, for example. These mammalian proteins having the same amino acid sequence as naturally occurring or endogenous corresponding mammalian hyaluronan synthase, are referred to by the name of the corresponding mammal. For example, as described herein, where the corresponding mammal is human, the protein is designated as a human hyaluronan synthase (HAS), such as recombinant human hyaluronan synthase produced in a suitable host cell.

"Functional variants" of mammalian hyaluronan synthase include functional fragments, functional mutant proteins, and/or functional fusion proteins. Generally, fragments or portions of mammalian hyaluronan synthase encompassed by the present invention include those having a deletion (i.e., one or more deletions) of an amino acid (i.e., one or more amino acids) relative to the mature mammalian hyaluronan synthase (such as N-terminal, C-terminal or internal deletions). Fragments or portions in which only contiguous amino acids have been deleted or in which non-contiguous amino acids have been deleted relative to mature mammalian hyaluronan synthase are also envisioned.

Generally, mutants or derivatives of mammalian hyaluronan synthase, encompassed by the present invention include natural or artificial variants differing by the addition, deletion and/or substitution of one or more contiguous or non-contiguous amino acid residues, or modified polypeptides in which one or more residues is modified, and mutants comprising one or more modified residues. Preferred mutants are natural or artificial variants of mammalian hyaluronan synthase differing by the addition, deletion and/ or substitution of one or more contiguous or non-contiguous amino acid residues.

A "functional fragment or portion", "functional mutant" and/or "functional fusion protein" of a mammalian hyaluronan synthase refers to an isolated and/or recombinant protein or oligopeptide which has at least one property, activity and/or function characteristic of a mammalian hyaluronan synthase, such as activity or function characteristic of a mammalian hyaluronan synthase (as defined herein), such as activity in the synthesis of hyaluronan and/or ability to confer cell adhesion by the lymphocyte receptor CD44.

Suitable fragments or mutants can be identified by screening. For example, the N-terminal, C-terminal, or internal regions of the protein can be deleted in a step-wise fashion and the resulting protein or polypeptide can be screened using a suitable binding or adhesion assay. Where the resulting protein displays activity in the assay, the resulting protein ("fragment") is functional. Information regarding the structure and function of other hyaluronan synthases (e.g., hasA, DG42), and of HAS as shown herein, provides a basis for dividing HAS into functional domains.

The term variant also encompasses fusion proteins, comprising a mammalian hyaluronan synthase (e.g., mature mammalian hyaluronan synthase) as a first moiety, linked to a second moiety not occurring in the mammalian hyaluronan synthaseas found in nature. Thus, the second moiety can be an amino acid, oligopeptide or polypeptide. The first moiety can be in an N-terminal location, C-terminal location or internal to the fusion protein. In one embodiment, the fusion protein comprises a mammalian hyaluronan synthase or portion thereof as the first moiety, and a second moiety comprising a linker sequence and affinity ligand (e.g., an enzyme, an antigen, epitope tag).

Examples of "mammalian hyaluronan synthase" proteins include proteins having an amino acid sequence as set forth or substantially as set forth in FIG. 2 (SEQ ID NO:2) and functional portions thereof. In a preferred embodiment, a mammalian hyaluronan synthase or variant has an amino acid sequence which has at least about 50% identity, more preferably at least about 75% identity, and still more preferably at least about 90% identity, to the protein shown in FIG. 2 (SEQ ID NO:2).

Method of Producing Recombinant Proteins

Another aspect of the invention relates to a method of producing a mammalian hyaluronan synthase or variant (e.g., portion) thereof. Recombinant protein can be obtained, for example, by the expression of a recombinant DNA molecule encoding a mammalian hyaluronan synthase or variant thereof in a suitable host cell, for example.

Constructs suitable for the expression of a mammalian hyaluronan synthase or variant thereof are also provided. The constructs can be introduced into a suitable host cell, and cells which express a recombinant mammalian hyaluronan synthase or variant thereof, can be produced and maintained in culture. Such cells are useful for a variety of purposes, and can be used in the production of protein for characterization, isolation and/or purification, (e.g., affinity purification), and as immunogens, for instance. Suitable host cells can be procaryotic, including bacterial cells such as *E. coli*, *B. subtilis* and or other suitable bacteria (e.g., Streptococci) or eucaryotic, such as fungal or yeast cells (e.g., *Pichia pastoris*, *Aspergillus species*, *Saccharomyces cerevisiae*, *Schizosaccharomyces pombe*, *Neurospora crassa*), or other lower eucaryotic cells, and cells of higher eucaryotes such as those from insects (e.g., Sf9 insect cells) or mammals (e.g., Chinese hamster ovary cells (CHO), COS cells, HuT 78 cells, 293 cells). (See, e.g., Ausubel, F. M. et al., eds. *Current Protocols in Molecular Biology*, Greene Publishing Associates and John Wiley & Sons Inc., (1993)).

Host cells which produce a recombinant mammalian hyaluronan synthase or variants thereof can be produced as follows. For example, a nucleic acid encoding all or part of the coding sequence for the desired protein can be inserted into a nucleic acid vector, e.g., a DNA vector, such as a plasmid, virus or other suitable replicon for expression. A variety of vectors are available, including vectors which are maintained in single copy or multiple copy, or which become integrated into the host cell chromosome.

The transcriptional and/or translational signals of a mammalian hyaluronan synthase gene can be used to direct expression. Alternatively, suitable expression vectors for the expression of a nucleic acid encoding all or part of the coding sequence of the desired protein are available. Suitable expression vectors can contain a number of components, including, but not limited to one or more of the following: an origin of replication; a selectable marker gene; one or more expression control elements, such as a transcriptional control element (e.g., a promoter, an enhancer, terminator), and/or one or more translation signals; a signal sequence or leader sequence for membrane targeting or secretion (of mammalian origin or from a heterologous mammal or non-mammalian species). In a construct, a signal sequence can be provided by the vector, the mammalian hyaluronan synthase coding sequence, or other source.

A promoter can be provided for expression in a suitable host cell. Promoters can be constitutive or inducible. The promoter is operably linked to a nucleic acid encoding the mammalian hyaluronan synthase or variant thereof, and is capable of directing expression of the encoded polypeptide in the host cell. A variety of suitable promoters for procaryotic (e.g., lac, tac, T3, T7 promoters for *E. coli*) and eucaryotic (e.g., yeast alcohol dehydrogenase (ADH1), SV40, CMV) hosts are available.

In addition, the expression vectors typically comprise a selectable marker for selection of host cells carrying the vector, and in the case of a replicable expression vector, an origin of replication. Genes encoding products which confer antibiotic or drug resistance are common selectable markers and may be used in procaryotic (e.g., β-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. The present invention also relates to cells carrying these expression vectors.

For example, a nucleic acid encoding a mammalian hyaluronan synthase or variant thereof can be incorporated into a vector, operably linked to one or more expression control elements, and the construct can be introduced into host cells which are maintained under conditions suitable for expression, whereby the encoded polypeptide is produced. The construct can be introduced into cells by a method appropriate to the host cell selected (e.g., transformation, transfection, electroporation, infection). For production of a protein, host cells comprising the construct are maintained under conditions appropriate for expression, (e.g., in the presence of inducer, suitable media supplemented with appropriate salts, growth factors, antibiotic, nutritional supplements, etc.). The encoded protein (e.g., human hyaluronan synthase) can be isolated from the host cells or medium.

Fusion proteins can also be produced in this manner. For example, some embodiments can be produced by the insertion of a mammalian hyaluronan synthase cDNA or portion thereof into a suitable expression vector, such as Bluescript®II SK +/− (Stratagene), pGEX-4T-2 (Pharmacia), pcDNA-3 (Invitrogen) and pET-15b (Novagen). The resulting construct can then be introduced into a suitable host cell for expression. Upon expression, fusion protein can be isolated or purified from a cell lysate by means of a suitable affinity matrix (see e.g., *Current Protocols in Molecular Biology* (Ausubel, F. M. et al., eds., Vol. 2, Suppl. 26, pp. 16.4.1–16.7.8 (1991)). In addition, affinity labels provide a means of detecting a fusion protein. For example, the cell surface expression or presence in a particular cell fraction of a fusion protein comprising an antigen or epitope affinity label can be detected by means of an appropriate antibody.

Nucleic Acids, Constructs and Vectors

The present invention relates to isolated and/or recombinant (including, e.g., essentially pure) nucleic acids (e.g., polynucleotides) having sequences which encode a mammalian hyaluronan synthase or variant thereof as described herein.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated (see e.g., Daugherty, B. L. et al., *Nucleic Acids Res.*, 19(9):2471–2476 (1991); Lewis, A. P. and J. S. Crowe, *Gene*, 101: 297–302 (1991)). Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

In one embodiment, the nucleic acid or portion thereof encodes a protein or polypeptide having at least one property, activity or function characteristic of a mammalian hyaluronan synthase (as defined herein), such as activity or function characteristic of a mammalian hyaluronan synthase (as defined herein), such as activity in the synthesis of hyaluronan and/or ability to mediate cell adhesion by the lymphocyte receptor CD44.

The present invention also relates more specifically to isolated and/or recombinant nucleic acids or a portion thereof having sequences which encode mammalian hyaluronan synthase or variants thereof.

The invention relates to isolated and/or recombinant nucleic acids that are characterized by:

(1) their ability to hybridize to (a) a nucleic acid encoding a mammalian hyaluronan synthase, such as a nucleic acid having a nucleotide sequence as set forth or substantially as set forth in FIG. 2 (SEQ ID NO:1); (b) the complement of (a); or (c) portions of either of the foregoing (e.g., a portion comprising the open reading frame); or (2) by their ability to encode a polypeptide having the amino acid sequence of a mammalian hyaluronan synthase (e.g., SEQ ID NO:2); or (3) by both characteristics.

In one embodiment, the nucleic acid shares at least about 50% nucleotide sequence similarity to the nucleotide sequences shown in FIG. 2 (SEQ ID NO:1). More preferably, the nucleic acid shares at least about 75% nucleotide sequence similarity, and still more preferably, at least about 90% nucleotide sequence similarity, to the sequence shown in FIG. 2 (SEQ ID NO:1).

Isolated and/or recombinant nucleic acids meeting these criteria comprise nucleic acids having sequences identical to sequences of naturally occurring mammalian hyaluronan synthase or variants of the naturally occurring sequences. Such variants include mutants differing by the addition, deletion or substitution of one or more residues, modified nucleic acids in which one or more residues are modified (e.g., DNA or RNA analogs), and mutants comprising one or more modified residues.

A nucleic acid of the present invention may be in the form of RNA or in the form of DNA (e.g., cDNA, genomic DNA, and synthetic DNA). The DNA may be double-stranded or single-stranded, and if single stranded may be the coding strand or non-coding (anti-sense) strand. The coding sequence which encodes the mature polypeptide may be identical to the coding sequence shown in FIG. 2 (SEQ ID NO:1) or that of the cDNA in clone 30C or may be a different coding sequence which coding sequence, as a result of the redundancy or degeneracy of the genetic code, encodes the same, mature polypeptides as the DNA of FIG. 2 (SEQ ID NO:2) or the cDNA in clone 30C.

The polynucleotide which encodes a mature polypeptide encoded by the cDNA of clone 30C may include: only the coding sequence of a mature polypeptide; the coding sequence for a mature polypeptide and additional coding sequence such as a leader or secretory sequence; the coding sequence for a mature polypeptide (and optionally additional coding sequence) and non-coding sequence, such as introns or non-coding sequence 5' and/or 3' of the coding sequence.

Nucleic acids of the present invention, including those which hybridize to a selected nucleic acid as described above, can be detected or isolated under high stringency conditions or moderate stringency conditions, for example. "High stringency conditions" and "moderate stringency conditions" for nucleic acid hybridizations are explained at pages 2.10.1–2.10.16 (see particularly 2.10.8–11) and pages 6.3.1–6 in *Current Protocols in Molecular Biology* (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, and depend in part upon the characteristics of the known nucleic acid (e.g., DNA) and the other nucleic acids to be assessed for hybridization thereto.

Isolated and/or recombinant nucleic acids that are characterized by their ability to hybridize (e.g., under high or moderate stringency conditions) to (a) a nucleic acid encoding a mammalian hyaluronan synthase (for example, the nucleic acid depicted in FIG. 2 (SEQ ID NO:1); (b) the complement of the nucleic acids of (a), (c) or a portion thereof, can also encode a protein or polypeptide having at least one property, activity or function characteristic of a mammalian hyaluronan synthase (as defined herein), such as activity in the synthesis of hyaluronan and/or ability to mediate cell adhesion by the lymphocyte receptor CD44, and in a preferred embodiment encode polypeptides which retain substantially the same biological function or activity as the mature polypeptide encoded by the cDNA of FIG. 2 (SEQ ID NO:1) or the cDNA of clone 30C.

Nucleic acids of the present invention can be used in the production of proteins or polypeptides. For example, a nucleic acid (e.g., DNA) encoding a mammalian hyaluronan synthase can be incorporated into various constructs and vectors created for further manipulation of sequences or for production of the encoded polypeptide in suitable host cells as described above.

A further embodiment of the invention is antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In a particular embodiment, the antisense nucleic acid is wholly or partially complementary to and can hybridize with a target nucleic acid, wherein the target nucleic acid can hybridize to a nucleic acid having the sequence of the complement of the strand shown in FIG. 2 (SEQ ID NO:1). For example, antisense nucleic acid can be complementary to a target nucleic acid having the sequence shown as the open reading frame in FIG. 2 (SEQ ID NO:1) or to a portion thereof sufficient to allow hybridization. In another embodiment, the antisense nucleic acid is wholly or partially complementary to and can hybridize with a target nucleic acid which encodes a mammalian hyaluronan synthase.

The nucleic acids can also be used as probes (e.g., in in situ hybridization) to assess associations between inflammatory settings (e.g., rheumatoid arthritis, osteoarthritis, liver cirrhosis, Werner's syndrome, renal failure and psoriasis) and increased expression of mammalian hyaluronan synthase in affected tissues or serum. The nucleic acids can also be used as probes to detect and/or isolate (e.g., by hybridization with RNA or DNA) polymorphic or allelic variants, for example, in a sample (e.g., inflamed tissue) obtained from a host (e.g. mammalian). Moreover, the presence or frequency of a particular variant in a sample(s) obtained from one or more affected hosts, as compared with a sample(s) from normal host(s), can be indicative of an association between an inflammatory setting and a particular variant, which in turn can be used in the diagnosis of the condition.

As described in the exemplification, functional expression cloning was used to identify a cDNA encoding human hyaluronan synthase, and it was demonstrated that this gene can confer activity both in the synthesis of hyaluronan and as a mediator of cell adhesion by the lymphocyte receptor CD44. A human hyaluronan synthase (HAS) cDNA was isolated by a functional expression cloning approach. Transfection of CHO cells conferred hyaluronidase sensitive adhesiveness of a mucosal T cell line via the lymphocyte hyaluronan receptor, CD44, as well as increased hyaluronan levels in the cultures of transfected cells. The HAS amino acid sequence shows homology to the hasA gene product of *Streptococcus pyogenes* and a putative glycosaminoglycan synthetase from *xenopus laevis*. Expression of HAS message parallels tissues where high levels of hyaluronan synthesis occur, indicating that transcription of synthase mRNA is a critical component of hyaluronate synthesis.

Utilities

Mammalian hyaluronan synthases of the present invention can be used to produce hyaluronan. Hyaluronan has a variety of uses, including use in cosmetics and pharmaceuticals (see e.g., EPO,443,043 B1 and U.S. Pat. No. 5,015,577 the teachings of which are each incorporated herein by reference). Hyaluronan or pharmaceutical compositions comprising hyaluronan are useful for treating wounds or surgical incisions and can reduce or prevent hypertrophic scars and keloid formation, and in eye surgery as a replacement for vitreous fluid, for example.

For example, a mammalian hyaluronan synthase can be expressed in a suitable host cell under conditions appropriate for production of hyaluronan to occur (e.g., in suitable medium comprising any required precursors). Isolated or purified hyaluronan synthase can also be used to prepare hyaluronan from precursors (e.g., UDP-glucuronic acid and UDP-N-aceytl-glucosamine).

The present invention also provides antibodies which (1) can bind a "mammalian hyaluronan synthase" in vitro and/or in vivo; and/or (2) can inhibit an activity or function characteristic of a "mammalian hyaluronan synthase", such as hyaluronan synthesis. Preferably the antibodies are capable of selective binding of mammalian hyaluronan synthase in vitro and/or in vivo (e.g., bind selectively to mammalian hyaluronan synthase expressed in ovary and/or spleen, thymus, prostate, etc. (e.g., as assessed immunohistologically)).

Preferably, the antibodies can bind a mammalian (e.g. human) hyaluronan synthase with high affinity (for example, a Ka in the range of about 1–10 nM, or a Kd in the range of about $1 \times 10^{-8}$ to $1 \times 10^{-10}$ mol$^{-1}$).

The antibodies of the present invention are useful in a variety of applications, including processes, research, diagnostic and therapeutic applications. For instance, they can be used to isolate and/or purify mammalian hyaluronan synthase or variants thereof (e.g., by affinity purification or other suitable methods), and to study mammalian hyaluronan synthase structure (e.g., conformation) and function.

The antibodies of the present invention can also be used to modulate mammalian hyaluronan synthase function in diagnostic (e.g., in vitro) or therapeutic applications. For instance, antibodies can act as inhibitors of (reduce or prevent) hyaluronan synthesis, thereby inhibiting process mediated by hyaluronan such as cell adhesion and metastasis.

In addition, antibodies of the present invention can be used to detect and/or measure the level of a mammalian hyaluronan synthase in a sample (e.g., tissues or body fluids, such as an inflammatory exudate, blood, serum, bowel fluid, or on cells transfected with a nucleic acid of the present invention). For example, a sample (e.g., tissue and/or fluid) can be obtained from a host (e.g., mammalian) and a suitable immunological method can be used to detect and/or measure mammalian hyaluronan synthase levels, including methods such as enzyme-linked immunosorbent assays (ELISA), including chemiluminescence assays, radioimmunoassay, and immunohistology. In one embodiment, a method of detecting a selected mammalian hyaluronan synthase in a sample is provided, comprising contacting a sample with an antibody which binds an isolated mammalian hyaluronan synthase under conditions suitable for specific binding of said antibody to the selected mammalian hyaluronan synthase, and detecting antibody-mammalian hyaluronan synthase complexes which are formed.

In an application of the method, antibodies reactive with a mammalian hyaluronan synthase can be used to analyze normal versus inflamed tissues in mammals for mammalian hyaluronan synthase reactivity and/or expression (e.g., immunohistologically). Thus, the antibodies of the present invention permit immunological methods of assessment of expression of primate (e.g., human mammalian hyaluronan synthase) in normal versus inflamed tissues, through which the presence of disease, disease progress and/or the efficacy of anti-mammalian hyaluronan synthase therapy in inflammatory disease can be assessed.

An antibody can be administered in an effective amount which inhibits mammalian hyaluronan synthase activity. For therapy, an effective amount will be sufficient to achieve the desired therapeutic and/or prophylactic effect (such as an amount sufficient to reduce or prevent mammalian hyaluronan synthase-mediated hyaluronan synthesis). The antibody can be administered in a single dose or multiple doses. The dosage can be determined by methods known in the art and is dependent, for example, upon the individual's age, sensitivity, tolerance and overall well-being. Suitable dosages for antibodies can be from 0.1–1.0 mg/kg body weight per treatment.

According to the method, an antibody can be administered to an individual (e.g., a human) alone or in conjunction with another agent (administered before, along with or subsequent to administration of the additional agent).

A variety of routes of administration are possible including, but not necessarily limited to parenteral (e.g., intravenous, intraarterial, intramuscular, subcutaneous injection), oral (e.g., dietary), topical, inhalation (e.g., intrabronchial, intranasal or oral inhalation, intranasal drops), or rectal, depending on the disease or condition to be treated. Parenteral administration is a preferred mode of administration.

Formulation will vary according to the route of administration selected (e.g., solution, emulsion, capsule). An appropriate composition comprising the antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Science*, 16th Edition, Mack, Ed. 1980). For inhalation, the compound can be solubilized and loaded into a suitable dispenser for administration (e.g., an atomizer, nebulizer or pressurized aerosol dispenser).

Exemplification

Plasmids, Monoclonal Antibodies and Cell Lines

The following plasmids were used as controls in expression cloning and for functional adhesion assays: pSV-SPORT-1 (GIBCO, Gaithersburg, Md.) or pcDNA3 (Invitrogen, San Diego, Calif.) controls and murine MAdCAM-1 in pCDM8 (pCDMAD-7 (Briskin, M. J., *Nature* 363:461–464 (1993)). Monoclonal antibodies used were anti-murine CD-44 TJB1.7 (a gift from T. Yoshino and E. Butcher, Stanford, Calif.); anti-murine MAdCAM-1 MECA-367 (Streeter, P. R. et al., *Nature* 331:41–46 (1988)); anti-human VCAM-1 2G7 (Graber, N. *J. Immunol.* (145):819 (1990)); anti-murine β7 FIB 504 (Andrew, D. P. et al., *J. Immunol.* 153:3847–3861 (1994)); and anti-murine α4 PS/2 (Miyake, K. *J. Exp. Med.* 173:599–607 (1991)). Cell lines used for expression cloning and functional adhesion assays were: CHO/P (Heffernan, M. and Dennis, J. D. *Nucl. Acids Res.* 19:85 (1991)) and the murine T cell lymphoma TK1 (Butcher, E. C. et al., *Eur. J. Immunol.* 10:556–561 (1980)).

cDNA Synthesis and Library Construction mRNA was isolated from human lymph nodes using standard procedures previously described (Briskin, M. J., *Nature* 363:461–464 (1993)). cDNA was synthesized using the Superscript™ lambda system in conjunction with the pSV-SPORT-1 vector (Gibco, Gaithersburg, Md.) essentially using the manufacturer's protocol. The highest molecular weight fractions (>1.5 kb) of cDNA were ligated into the pSV-SPORT-1 vector and plated in pools at a density of 5,000 clones/plate on 100 LB agar plates with ampicillin (50 μg/ml). After incubation overnight, plasmid DNAs were purified from each plate individually by use of QIAprep spin columns (QIAGEN, Chatsworth, Calif.) according to manufacturer's instructions.

Expression Cloning

CHO/P cells were seeded into 24 well plates approximately 24 hours prior to transfection at a density of 40,000 cells/well. DNAs were transiently transfected using the LipofectAMINE™ reagent (GIBCO, Gaithersburg, Md.) as recently described (Shyjan, A. M. et al., *J. Immunol.*, 156:2851–2857 (1996)).

For the adhesion assays in the expression cloning screen, TK1 cells are resuspended at a density of $2 \times 10^6$/ml in a cell binding assay buffer previously described (Shyjan, A. M. et al., *J. Immunol.* in press (1996)). After incubation at 4° C. for 15 minutes, 0.25 ml of the TK1 cell suspension ($5 \times 10^5$ TK1 cells) was added to each well and incubation on a rocking platform was continued for an additional 30 minutes at 4° C. Plates were washed by gently inverting in a large beaker of phosphate buffered saline (PBS) followed by inversion in a beaker of PBS with 1.5% glutaraldehyde for fixation for a minimum of 1 hour. Wells were then examined microscopically (10×objective) for rosetting of TK1 cells mediated by the pools of cDNA clones. Pools yielding one or more TK1 rosettes were further subfractionated three times until individual colonies could be assayed and the clones conferring adhesion of the TK1 cells were identified.

Functional Adhesion Assays

Assays with purified clones were similar to those performed in expression cloning with the following exception: as several wells were to be transfected for antibody inhibition studies, a master liposome mix with multiples of the wells to be transfected was first made for each plasmid. On the day of the assay monoclonal antibodies were incubated with cells at 20 μg/ml or supernatants (undiluted) at 4° C. for 15 minutes prior to the start of the assay.

For adhesion assays with hyaluronan, human umbilical cord hyaluronan (Calbiochem, San Diego, Calif.) was diluted to 5 mg/ml in PBS. Streptomyces hyaluronidase (Calbiochem, San Diego, Calif.) was diluted to 20 TRU/ml in HBSS. TK1 cells were resuspended in HBSS containing 2 mM $CaCl_2$, 2 mM $MgCl_2$, 2% serum and 20 mM HEPES at $10^6$ cells/ml. Wells of 24-well plates were coated with 200 μl of hyaluronan and stored at 4° C. overnight. Wells were rinsed with 0.5 ml PBS three times, and were treated with 0.25 ml Streptomyces hyaluronidase at final concentrations of 0, 5, 10 and 20 TRU/ml for 1 hour at 37° C. Wells were rinsed three times with 0.5 ml PBS, blocked with 0.5 ml serum for 1 hour on ice and then rinsed three times with 0.5 ml PBS. TK1 cells (0.5 ml) were added to each well and plates were incubated with shaking at 4° C. for 20 minutes.

For assessment of hyaluronate mediated binding to CHO/P cells, the transfectants were rinsed with 0.5 ml PBS three times. Individual wells were treated with 250 μl Streptomyces hyaluronidase at 0, 5, 10 and 20 TRU/ml (final concentrations) for 1 hour at 37° C. Transfectants were rinsed three times with 0.5 ml PBS. TK1 cells (0.5 ml in the same buffer as described above) were added to each well and plates were incubated with shaking at 4° C. for 30 minutes. Wells were rinsed with 0.5 ml PBS three times and viewed under the light microscope. Assays were fixed as described above and analyzed by examination of multiple fields and counting both lymphocytes and CHO cells at 10×magnification.

Measurement of Hyaluronic Acid Biosynthesis in CHO Cell Transfectants $0.5 \times 10^6$ CHO cells seeded in 100 mm plates were transfected with Lipofectamine reagent according to manufacaturer's instructions. Tranfections utilized 20 µg of HAS cDNA in pcDNA3 (Invitrogen, San Diego, Calif.) and 160 µl of lipofectamine reagent. Clone 30C was digested with EcoRI and NotI and the insert released thereby was cloned into the ECORI and NotI sites of pcDNA3. Transformants of *E. coli* XL-1 Blue (Stratagene) or DH1OB (Gibco) containing the resulting construct were obtained. Approximately 72 hours after transfection, 440 µg/ml of G418 was added in fresh media. After the transfected and control (non transfected) cells had reached subconfluency, the media was replaced with fresh complete media containing 5 mCi/ml D-[6-$^3$H] glucosamine hydrochloride (New England Nuclear, Boston, Mass., specific activity 33.3 ci/ml, concentration 1 mCi/ml), a precursor of sulfated glucosaminoglycans such as hyaluronan. The amounts of synthesized hyaluronan in transfected and control CHO cells were determined after 48 hours of incubation at 37° C. as follows. Media was collected and the cell layers were combined with the corresponding media. Aliquots from each sample were incubated overnight at 37° C. in the presence or absence of Streptomyces hyaluronidase. Then the samples were applied on sephadex G-50 superfine columns (100×100 mm) which were equilibrated with 0.05 M sodium acetate, pH 6.0 containing 0.2M NaCl. Newly synthesized [$^3$H] hyaluronan was determined as the Streptomyces sensitive radioactivity.

DNA Sequencing

Plasmids were sequenced on both strands using oligonucleotide primers and the sequenase™ 7-deaza-dGTP DNA sequencing kit with sequenase version 2.0 T7 DNA polymerase (United States Biochemical, Cleveland, Ohio) and $^{35}$SdCTP (Amersham Life Science, Arlington Heights, Ill. and New England Nuclear, Boston, Mass.) using manufacturer's instructions.

Northern and Southern Blot Analysis

Northern blots used were human multiple tissue northerns I and II (Clontech, Palo Alto, Calif.). Hybridization was performed with ExpressHyb (Clontech) solution, using manufacturer's instructions except that a final wash at high stringency (0.1×SSC, 0.1% SDS, 65° C.) for 30 min was added. A commercially prepared southern blot (Human GENO-BLOT) (Clontech, Palo Alto, Calif.) was hybridized as described for the Northern blot with the exception that an initial wash at 50° C. was exposed and then the blot was subsequently washed at 65° C. and exposed again. cDNA's were labelled with $\alpha^{32}$P-dCTP by priming with random hexamers. After washing, filters were exposed to Kodak XAR film with an intensifying screen.

Results and Discussion

An expression cloning system was developed to isolate cDNA clones that encode proteins that confer adhesion of the murine T cell lymphoma TK1 (Butcher, E. C. et al., *Eur. J. Immunol.* 10:556–561 (1980)). A human mesenteric lymph node expression library was constructed that, upon transfection into CHO/P cells, yielded a cDNA clone, called 30C, that mediated resetting of TK1 cells to some of the CHO/P transfectants. Transformants of *E. coli* XL-1 Blue (Stratagene) containing Clone 30C were obtained. In order to understand the nature of the observed interaction, the adhesion assay after pre-incubation of the TK1 line with several antibodies to adhesion receptors known to be expressed on TK1 cells was repeated. Binding could be completely inhibited by pre-incubation of TK1 cells with an antibody to CD44 (Table 1), while other antibodies (anti-α4 and anti-β7 integrins (Andrew, D. P. et al., *J. Immunol.* 153:3847–3861 (1994); Miyake, K. *J. Exp. Med.* 173:599–607 (1991)) had no effect.

TABLE 1

Adhesion of TK1 cells to clone 30C transfectants.
TK1 cells bind to CHO/P cells transiently transfected with clone 30C. Binding is blocked by pretreatment of the transfectants with hyaluronidase or pretreatment of TK1 cells with anti-CD44 MAb TJB1.7. Similar results are seen with binding to immobilized hyaluronate, while TK1 cells do not bind mock transfectants. A score of "−" indicates that no TK1 cells (above controls) were observed in those wells while "+++" indicates TK1 rosetting on transfectants (>5 TK1 cells/CHO/P transfectant) or a monolayer of cells binding to immobilized hyaluronate. Assays were all repeated three times with similar results.

| Cells/Matrix | TK1 Cell | TK1 Binding after hyaluronidase | TK1 Binding after anti-CD44 MAb TJB1.7 | TK1 Binding after anti-a4 MAb PS/2 |
|---|---|---|---|---|
| HAS Transfectants | +++ | − | − | +++ |
| Mock Transfectants | − | − | − | − |
| Hyaluronate | +++ | − | − | +++ |

Figure 1B:
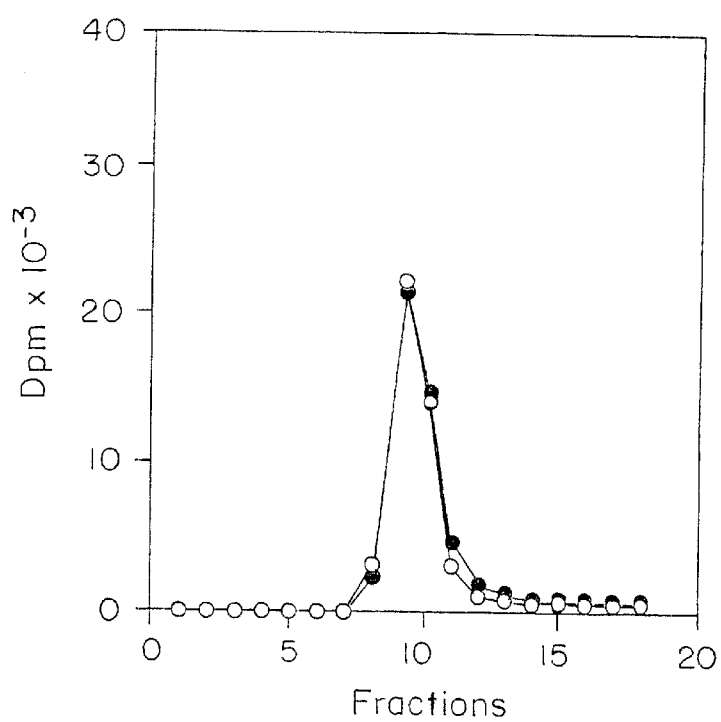
FIG. 1B is a graph illustrating that CHO cells not transfected with human hyaluronan synthase cDNA produce very little high molecular weight streptomyces hyaluronidase-sensitive material.

As CD44 is known to be a hyaluronan receptor (Aruffo, A., et al., *Cell* 61:1303–1313 (1990); Culty, M. et al.,*J. Cell. Biol.,* 111:2765–2774 (1990); Miyake, K. et al.,*J. Exp. Med.* 172:69–75 (1990)), it was investigated whether the isolated cDNA encoded a novel CD44 ligand or, alternatively, was involved in de novo synthesis of hyaluronan. Hyaluronidase pretreatment completely abrogated TK1 binding to the transfectants as well as to hyaluronan controls (Table 1), indicating that the cloned cDNA mediated synthesis of HA. Finally, CHO cells were stably transfected with the 30C cDNA and assessed for their ability to mediate hyaluronan biosynthesis (FIGS. 1A,B). Whereas, untranfected cells produced very little high molecular weight Streptomyces hyaluronaidase-sensitive material (FIG. 1B), cell cultures transfected with 30C cDNA produced a substantial amount of hyaluronan (FIG. 1A).

The cDNA encoding clone 30C is 2116 nucleotides in length (FIG. 2) with a short 5' untranslated region of 35 bp and a longer 3' untranslated region of 347 bp. From the first ATG, a predicted open reading frame of 1734 bp yielding a protein of 578 amino acid residues is present. Genbank searches of the nucleotide and protein sequences revealed significant homology with the hasA gene of *Streptococcus pyogenes* (DeAngelis, J.P.a.P.H.W., *J. Biol. Chem.* 268:19181–19184 (1993)), which was reported to be a hyaluronan synthase (FIGS. 3A—3B and FIG. 3C) and a sequence from Xenopus laevis called DG42 (FIGS. 3A—3B and FIG. 3C) which has also been speculated to be a glycosaminoglycan synthetase (Rosa, F. et al., *Develop. Biol.* 129:114–123 (1988)). Amino acid sequence identities between the predicted protein and these sequences were 22% and 54%, respectively. Significant similarity was also observed with other membrane associated proteins with N-acetylyglucosylamino transferase activity including NodC from Rhizobium and three chitin synthases from Saccharomyces (Chs) (DeAngelis, P. L. et al., *Biochem. and Biophys. Res. Comm.* 199:1–10 (1994)). The similarities observed, coupled with the functional adhesion indicate that clone 30C encodes a human homolog of hyaluronan synthase (HS). Using nomenclature based on the streptococcus gene locus, this human gene encoding hyaluronan synthase is designated HAS.

Figure 3C:
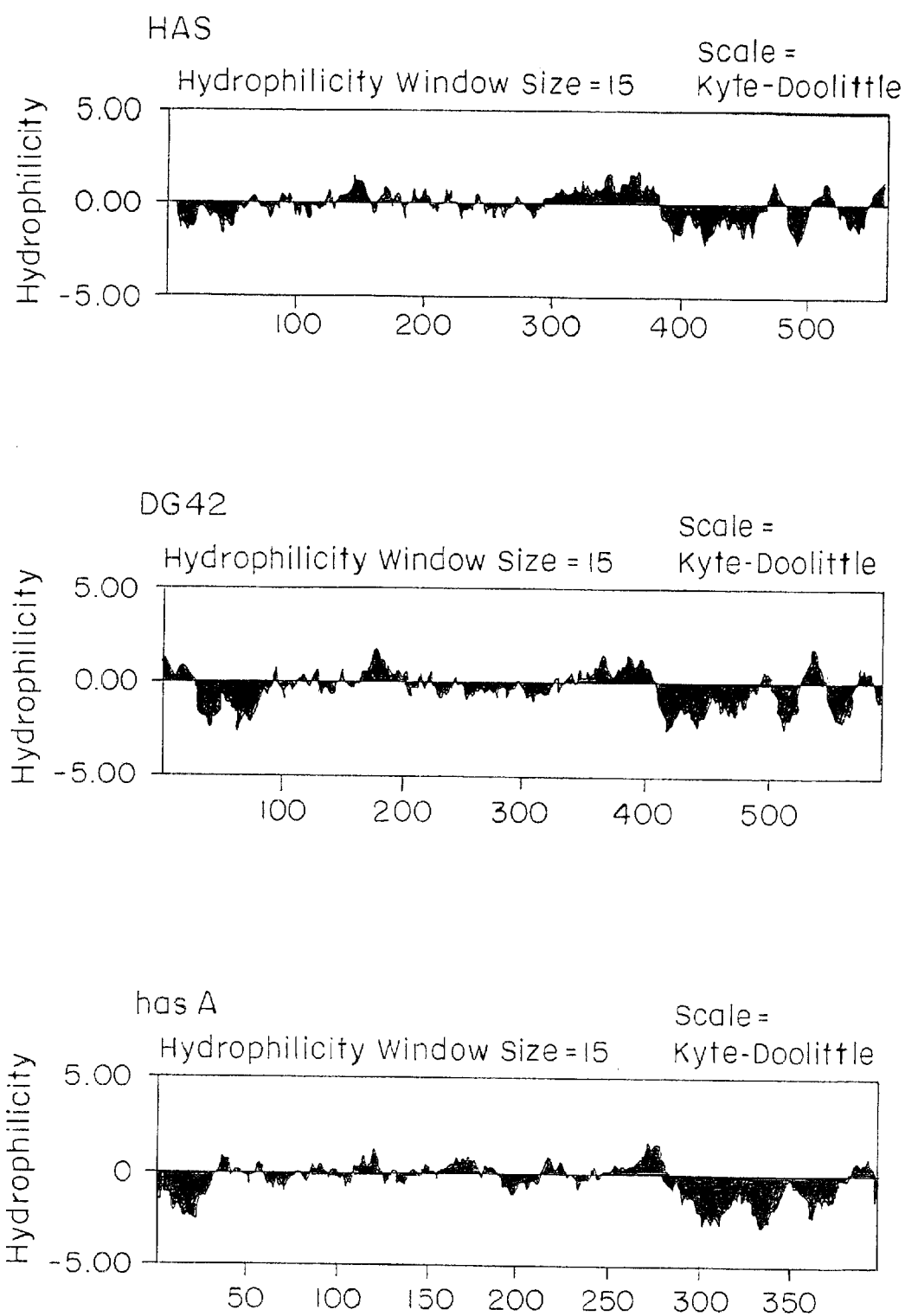
FIG. 3C is a comparison of Kyte-Doolittle hydrophilicity profiles of human hyaluronan synthase, DG42 and hasA.

The predicted molecular mass of the HAS protein is 64,793 daltons. Hydrophilicity (Kyte-Doolitle) analysis predicts a membrane protein with several hydrophobic regions that would be predicted to span the cell membrane at least four times (FIGS. 3A–3D). This prediction is in agreement with labeling studies which suggested that hyaluronan synthase is associated with the plasma membrane (Prehm, P., *Biochem. J.* 220:597–600 (1984); Phillipson, L. H. and Schwartz, N. B. *J. Biol. Chem.* 259:5017–5023 (1984); Klewes, L. et al., *Biochem J.* 290:791–795 (1993); O'Regan, M. et al., *Int. J. Biol. Macromol.* 16:283–286 (1994)). Conservation of secondary structure between hasA, DG42 and HAS, is indicated by similar hydrophilicity plots. The approximate locations of these regions, with respect to HAS, are shown in the alignment in FIGS. 3A—3B and their representative hydrophilicity plots are shown in FIG. 3C.

Figure 3D:
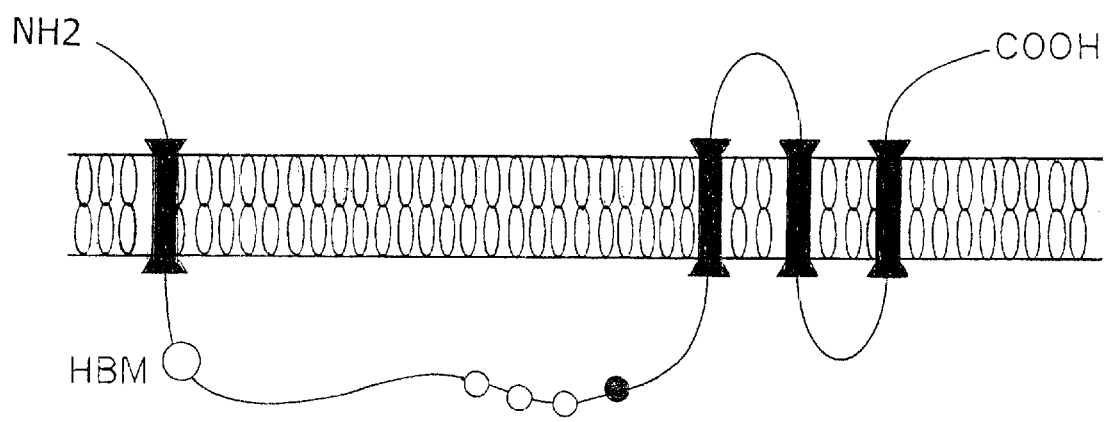
FIG. 3D is a proposed structure of human hyaluronan synthase, indicating approximate boundaries of transmembrane regions and intra- and extracellular loops; a hyaluronan binding motif (HBM), $B(X_7)B$, is indicated at the amino portion of a large predicted intracellular loop; approximate locations of protein kinase C consensus sites are indicated by open circles, while a single cAMP dependent kinase site is shown as a filled circle.

The estimated number of transmembrane segments would suggest a structure with a small N-terminal extracellular domain followed by a long intracellular loop and then three more transmembrane regions to yield one more small extracellular loop, a small intracellular loop followed by a C-terminal extracellular extension (FIG. 3D). Such a model, with the predominant portion of the protein located intracellularly would be consistent with studies indicating that hyaluronan biosynthesis occurs at the inner surface of the plasma membrane (Prehm, P. *Biochem. J.* 220:597–600 (1984); Phillipson, L. H., and Schwartz, N. B. *J. Biol. Chem* . 259:5017–5023 (1984)). This predicted large intracellular loop, is more highly conserved than the overall protein at 70% (vs 54%) when compared with DG42, which would imply conservation of a functional domain. Within the amino terminal portion of this domain lies a motif, designated $B(X_7)B$ (FIGS. 2 and 3D), where B is a basic amino acid (e.g., R, K) and X is any non-acidic residue. This motif has been found in both RHAMM, link protein and CD44, and mutagenesis studies has shown that this sequence is required for binding hyaluronan (Yang, B., et al., *EMBO* 13:286–296 (1994)). The presence of this putative hyaluronan binding motif (HBM) in HAS raises the possibility of a requirement of binding hyaluronan during its synthesis and prior to transport out of the cell.

Northern blots probed with the entire human cDNA, revealed a major transcript of 2.4 kb that was most highly expressed in ovary and also expressed at significant levels in spleen, thymus, prostate, testes and large intestine (FIG. 4A). In addition, a less abundant transcript of approximately 7 kb was also observed in these tissues and in addition to a faint 9 kb species only expressed in ovary. Extremely weak expression was observed in small intestine while peripheral blood leukocytes (PBL) were negative under the conditions used. Moderate expression was also observed in heart. The larger transcript observed might be a related gene in these tissues although a southern blot probed first with both full length and then a 3' region of HAS cDNA and washed at several temperatures shows a simple banding pattern suggestive of a single copy gene (FIG. 4B). It is therefore likely that these larger species represent unprocessed nuclear precursors, as opposed to related genes. The expression pattern observed is consistent with high levels of hyaluronan that are observed in lymphoid tissues, preovulatory follicles and in perivascular connective tissue and vessel walls of both atrium and ventricle (Edelstrom, G.A.B. et al., *Histochem. Cytochem.,* 39:1131–1135 (1991); Laurent, C. et al., *Cell Tissue Res.,* 263: 201–205 (1991)) and would indicate that synthesis of hyaluronan is at least partially regulated by transcriptional mechanisms. Interestingly, however, expression of HAS RNA was barely detectable in skeletal muscle under the conditions used, although histochemical analysis has shown ubiquitous distribution of hyaluronan in connective tissue and the septum dividing muscle fibers (Edelstrom, G.A.B. et al., *Histochem. Cytochem* 39:1131–1135 (1991); Laurent, C. et al., *Cell Tissue Res.* 263: 201–205 (1991)). This may indicate that turnover rates of hyaluronan may display great variation in different tissues.

Induction of synthase activity by growth factors has been shown to require protein synthesis and is mediated by a signaling pathway involving tyrosine phosphorylation and/or activation of protein kinase C (Heldin, P. et al., *Biochem. J.* 258, 919–922 (1992); Suzuki, M. et al., *Biochem. J.* 307:817–821 (1995)) as both PMA and inhibitors of phosphotyrosine phosphatases can induce hyaluronan synthesis. Serum alone can also induce synthase activity and this induction was blocked by protein kinase C inhibitors and cycloheximide. cAMP has also been implicated in activation and phosphorlyation of the synthase itself may play a key role in regulation of its activity (Klewes, L. and Prehm, P., *J. of Cell. Physiol.* 160:539–544 (1994)). Examination of hydrophilic regions of HAS reveals several conserved motifs which are potential substrates for protein kinase C and cAMP dependent kinases (FIGS. 2 and 3D) and are likely targets for future mutagenesis studies (Pearson, R. B., *Studies of protein kinase/phosphatase specificity using synthetic peptides.* Protein phosphorylation: A practical approach (Hardie, D. G., Ed.), Oxford University Press, Oxford (1993)). As observed, increased expression of the HAS gene in tissues that are known to produce large quantities of hyaluronan, it is likely that the regulation of hyaluronan synthesis is mediated by regulation of HAS gene transcription, in addition to complex regulatory circuits which involve both alterations in phosphorylation of the synthase or proteins associated with HAS.

Previously, a 52 kDa protein was isolated from a mouse/hamster hybridoma (B6 cells) that was initially reported to be a mammalian hyaluronan synthase (Klewes, L. et al., *Biochem J.* 290:791–795 (1993)). This protein was incapable of binding UDP-Glucuronic acid (UDP-[14C] GlcA) and UDP-N-acetyl glucosamine (UDP-[3H] GlcNAc) unless complexed to a 60 kDa protein, which may be the hyaluronan receptor (RHAMM) recently implicated in fibroblast migration and tumor metastasis (Turley, E. A. et al., *J. Cell Biol.,* 112:1041–1047 (1991)). This protein cross-reacted with antibodies against a putative synthase from *Streptococcus equisimilis.* The gene encoding this protein was cloned from a streptoccal library and shown to be related to proteins involved in oligopeptide processing and transport and showed no homology to the hasA gene sequence (O'Regan, M. et al., *Int. J. Biol. Macromol.* 16:283–286 (1994); Lansing, M. et al., *Biochem. J.* 289:179–184 (1993)). It is likely that the 52 kd protein isolated from the B6 line is a homolog to the streptococcal transport protein and not the synthase itself. The human hyaluronan synthase cDNA is therefore the first example of a mammalian gene responsible for synthesis of hyaluronan.

Studies in streptococci show that the machinery responsible for synthesis of hyaluronan is encoded in the has operon which consists of three genes hasA, B and C (Dougherty, B. P., and van de Rijn, I. *J. Biol. Chem.* 269:169–175 (1994); Dougherty, B. P., and van de Rijn, I. *J. Biol. Chem.* 268:7118–7124 (1993); Crater, D. L., and van de Rijn, I. *J. Biol. Chem.* 270:18452–18458 (1995)). It has been demonstrated that HAS is homologous to hasA which encodes hyaluronan synthase, along with a recently cloned cDNA encoding the murine synthase (Has) as well. The hasB and C loci encode UDP:Glc dehydrogenase and UDP-GLc pyrophosphorylase respectively (Dougherty, B. P., and van de Rijn, I. *J. Biol. Chem.* 269:169–175 (1994); Dougherty, B. P., and van de Rijn, I. *J. Biol. Chem.* 268:7118–7124 (1993); Crater, D. L., and van de Rijn, I. *J. Biol. Chem.* 270:18452–18458 (1995)). Also demonstrated herein is that transfection of the HAS cDNA into CHO cells is sufficient to mediate de novo synthesis of hyaluronan, which indicates that all of the other factors necessary for hyaluronan biosynthesis such as those encoded by hasB and C are possibly expressed in CHO cells. Recent data suggests that hyaluronan can also be synthesized upon transfection of the synthase into COS cells and a murine preB lymphoma which suggests that these backgrounds have endogenous UDP-GLc dehydrogenase and UDP-GLc phosphorylase and expression of HAS is then the most significant factor in regulating hyaluronan synthesis in mammalian cells. The identification of this cDNA will therefore assist further characterization of the molecular events resulting in synthesis of hyaluronan and its relationship to cellular migration in wound healing, tumor metastasis and leukocyte migration.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

I claim:

1. An isolated or recombinant nucleic acid which encodes a human hyaluronan synthase, wherein the nucleic acid sequence comprises SEQ ID NO: 1 or a portion thereof comprising the open reading frame.

2. An isolated or recombinant nucleic acid wherein the nucleic acid encodes the amino acid sequence of SEQ ID NO: 2.

3. A recombinant nucleic acid construct comprising a nucleic acid of claim 1.

4. A recombinant nucleic acid construct comprising a nucleic acid of claim 2.

5. The recombinant nucleic acid construct of claim 3 wherein the nucleic acid is operably linked to an expression control sequence.

6. A host cell comprising a recombinant nucleic acid of claim 1.

7. The host cell of claim 6 wherein the nucleic acid is operably linked to an expression control sequence, whereby mammalian hyaluronan synthase is expressed when the host cell is maintained under conditions suitable for expression.

8. A method for producing a mammalian hyaluronan synthase comprising:
   a) introducing into a host cell a nucleic acid construct comprising a nucleic acid selected from the group consisting of SEQ ID NO: 1 a portion thereof comprising the open reading frame, and a nucleic acid encoding SEQ ID NO:2 which encodes a mammalian hyaluronan synthase, whereby a recombinant host cell is produced having said coding sequence operably linked to at least one expression control sequence; and
   b) maintaining the host cells produced in step a) under conditions whereby the nucleic acid is expressed.

9. A method of producing hyaluronan comprising maintaining a host cell of claim 6 under conditions whereby hyaluronan is produced.

10. The method of claim 9, comprising isolating hyaluronan thereby produced.

11. The recombinant nucleic acid construct of claim 4 wherein the nucleic acid is operably linked to an expression control sequence.

12. A host cell comprising a recombinant nucleic acid of claim 2.

13. A method of producing hyaluronan comprising maintaining a host cell of claim 12 under conditions whereby hyaluronan is produced.

14. The method of claim 13, comprising isolating hyaluronan thereby produced.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 2116 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 36..1769

(xi) SEQUENCE DESCRIPTION: SEQ ID NO:1:

```
CGGAGAGAAG AGAGAGCCCG GCCAGACCCA CTGCG ATG AGA CAG CAG GAC GCG         53
                                     Met Arg Gln Gln Asp Ala
                                       1               5

CCC AAG CCC ACT CCT GCA GCC CGC CGC TGC TCC GGC CTG GCC CGG AGG       101
Pro Lys Pro Thr Pro Ala Ala Arg Arg Cys Ser Gly Leu Ala Arg Arg
         10                  15                  20

GTG CTG ACC ATC GCC TTC GCC CTG CTC ATC CTG GGC CTC ATG ACC TGG       149
Val Leu Thr Ile Ala Phe Ala Leu Leu Ile Leu Gly Leu Met Thr Trp
     25                  30                  35

GCC TAC GCC GCC GGG GTG CCG CTG GCC TCC GAT CGC TAC GGC CTC CTG       197
Ala Tyr Ala Ala Gly Val Pro Leu Ala Ser Asp Arg Tyr Gly Leu Leu
 40                  45                  50

GCC TTC GGC CTC TAC GGG GCC TTC CTT TCA GCG CAC CTG GTG GCG CAG       245
Ala Phe Gly Leu Tyr Gly Ala Phe Leu Ser Ala His Leu Val Ala Gln
 55                  60                  65                  70

AGC CTC TTC GCG TAC CTG GAG CAC CGG CGG GTG GCG GCG GCG GCG CGG       293
Ser Leu Phe Ala Tyr Leu Glu His Arg Arg Val Ala Ala Ala Ala Arg
                 75                  80                  85

GGG CCG CTG GAT GCA GCC ACC GCG CGC AGT GTG GCG CTG ACC ATC TCC       341
Gly Pro Leu Asp Ala Ala Thr Ala Arg Ser Val Ala Leu Thr Ile Ser
             90                  95                 100

GCC TAC CAG GAG GAC CCC GCG TAC CTG CGC CAG TGC CTG GCG TCC GCC       389
Ala Tyr Gln Glu Asp Pro Ala Tyr Leu Arg Gln Cys Leu Ala Ser Ala
        105                 110                 115
```

```
CGC GCC CTG CTG TAC CCG CGC GCG CGG CTG CGC GTC CTC ATG GTG GTG      437
Arg Ala Leu Leu Tyr Pro Arg Ala Arg Leu Arg Val Leu Met Val Val
    120                 125                 130

GAT GGC AAC CGC GCC GAG GAC CTC TAC ATG GTC GAC ATG TTC CGC GAG      485
Asp Gly Asn Arg Ala Glu Asp Leu Tyr Met Val Asp Met Phe Arg Glu
135                 140                 145                 150

GTC TTC GCT GAC GAG GAC CCC GCC ACG TAC GTG TGG GAC GGC AAC TAC      533
Val Phe Ala Asp Glu Asp Pro Ala Thr Tyr Val Trp Asp Gly Asn Tyr
                155                 160                 165

CAC CAG CCC TGG GAA CCC GCG GCG GCG GGC GCG GTG GGC GCC GGA GCC      581
His Gln Pro Trp Glu Pro Ala Ala Ala Gly Ala Val Gly Ala Gly Ala
            170                 175                 180

TAT CGG GAG GTG GAG GCG GAG GAT CCT GGG CGG CTG GCA GTG GAG GCG      629
Tyr Arg Glu Val Glu Ala Glu Asp Pro Gly Arg Leu Ala Val Glu Ala
        185                 190                 195

CTG GTG AGG ACT CGC AGG TGC GTG TGC GTG GCG CAG CGC TGG GGC GGC      677
Leu Val Arg Thr Arg Arg Cys Val Cys Val Ala Gln Arg Trp Gly Gly
    200                 205                 210

AAG CGC GAG GTC ATG TAC ACA GCC TTC AAG GCG CTC GGA GAT TCG GTG      725
Lys Arg Glu Val Met Tyr Thr Ala Phe Lys Ala Leu Gly Asp Ser Val
215                 220                 225                 230

GAC TAC GTG CAG GTC TGT GAC TCG GAC ACA AGG TTG GAC CCC ATG GCA      773
Asp Tyr Val Gln Val Cys Asp Ser Asp Thr Arg Leu Asp Pro Met Ala
                235                 240                 245

CTG CTG GAG CTC GTG CGG GTA CTG GAC GAG GAC CCC CGG GTA GGG GCT      821
Leu Leu Glu Leu Val Arg Val Leu Asp Glu Asp Pro Arg Val Gly Ala
            250                 255                 260

GTT GGT GGG GAC GTG CGG ATC CTT AAC CCT CTG GAC TCC TGG GTC AGC      869
Val Gly Gly Asp Val Arg Ile Leu Asn Pro Leu Asp Ser Trp Val Ser
        265                 270                 275

TTC CTA AGC AGC CTG CGA TAC TGG GTA GCC TTC AAT GTG GAG CGG GCT      917
Phe Leu Ser Ser Leu Arg Tyr Trp Val Ala Phe Asn Val Glu Arg Ala
    280                 285                 290

TGT CAG AGC TAC TTC CAC TGT GTA TCC TGC ATC AGC GGT CCT CTA GGC      965
Cys Gln Ser Tyr Phe His Cys Val Ser Cys Ile Ser Gly Pro Leu Gly
295                 300                 305                 310

CTA TAT AGG AAT AAC CTC TTG CAG CAG TTT CTT GAG GCC TGG TAC AAC     1013
Leu Tyr Arg Asn Asn Leu Leu Gln Gln Phe Leu Glu Ala Trp Tyr Asn
                315                 320                 325

CAG AAG TTC CTG GGT ACC CAC TGT ACT TTT GGG GAT GAC CGG CAC CTC     1061
Gln Lys Phe Leu Gly Thr His Cys Thr Phe Gly Asp Asp Arg His Leu
            330                 335                 340

ACC AAC CGC ATG CTC AGC ATG GGT TAT GCT ACC AAG TAC ACC TCC AGG     1109
Thr Asn Arg Met Leu Ser Met Gly Tyr Ala Thr Lys Tyr Thr Ser Arg
        345                 350                 355

TCC CGC TGC TAC TCA GAG ACG CCC TCG TCC TTC CTG CGG TGG CTG AGC     1157
Ser Arg Cys Tyr Ser Glu Thr Pro Ser Ser Phe Leu Arg Trp Leu Ser
    360                 365                 370

CAG CAG ACA CGC TGG TCC AAG TCG TAC TTC CGT GAG TGG CTG TAC AAC     1205
Gln Gln Thr Arg Trp Ser Lys Ser Tyr Phe Arg Glu Trp Leu Tyr Asn
375                 380                 385                 390

GCG CTC TGG TGG CAC CGG CAC CAT GCG TGG ATG ACC TAC GAG GCG GTG     1253
Ala Leu Trp Trp His Arg His His Ala Trp Met Thr Tyr Glu Ala Val
                395                 400                 405

GTC TCC GGC CTG TTC CCC TTC TTC GTG GCG GCC ACT GTG CTG CGT CTG     1301
Val Ser Gly Leu Phe Pro Phe Phe Val Ala Ala Thr Val Leu Arg Leu
            410                 415                 420

TTC TAC GCG GGC CGC CCT TGG GCG CTG CTG TGG GTG CTG CTG TGC GTG     1349
Phe Tyr Ala Gly Arg Pro Trp Ala Leu Leu Trp Val Leu Leu Cys Val
```

-continued

```
                425                 430                 435
CAG GGC GTG GCA CTG GCC AAG GCG GCC TTC GCG GCC TGG CTG CGG GGC    1397
Gln Gly Val Ala Leu Ala Lys Ala Ala Phe Ala Ala Trp Leu Arg Gly
        440                 445                 450

TGC CTG CGC ATG GTG CTT CTG TCG CTC TAC GCG CCC CTC TAC ATG TGT    1445
Cys Leu Arg Met Val Leu Leu Ser Leu Tyr Ala Pro Leu Tyr Met Cys
455                 460                 465                 470

GGC CTC CTG CCT GCC AAG TTC CTG GCG CTA GTC ACC ATG AAC CAG AGT    1493
Gly Leu Leu Pro Ala Lys Phe Leu Ala Leu Val Thr Met Asn Gln Ser
                475                 480                 485

GGC TGG GGC ACC TCG GGC CGG CGG AAG CTG GCC GCT AAC TAC GTC CCT    1541
Gly Trp Gly Thr Ser Gly Arg Arg Lys Leu Ala Ala Asn Tyr Val Pro
            490                 495                 500

CTG CTG CCC CTG GCG CTC TGG GCG CTG CTG CTG CTT GGG GGC CTG GTC    1589
Leu Leu Pro Leu Ala Leu Trp Ala Leu Leu Leu Leu Gly Gly Leu Val
        505                 510                 515

CGC AGC GTA GCA CAC GAG GCC AGG GCC GAC TGG AGC GGC CCT TCC CGC    1637
Arg Ser Val Ala His Glu Ala Arg Ala Asp Trp Ser Gly Pro Ser Arg
    520                 525                 530

GCA GCC GAG GCC TAC CAC TTG GCC GCG GGG GCC GGC GCC TAC GTG GGC    1685
Ala Ala Glu Ala Tyr His Leu Ala Ala Gly Ala Gly Ala Tyr Val Gly
535                 540                 545                 550

TAC TGG GTG GCC ATG TTG ACG CTG TAC TGG GTG GGC GTG CGG AGG CTT    1733
Tyr Trp Val Ala Met Leu Thr Leu Tyr Trp Val Gly Val Arg Arg Leu
                555                 560                 565

TGC CGG CGG CGG ACC GGG GGC TAC CGC GTC CAG GTG TGAGTCCAGC         1779
Cys Arg Arg Arg Thr Gly Gly Tyr Arg Val Gln Val
            570                 575

CACGCGGATG CCGCCTCAAG GGTCTTCAGG GGAGGCCAGA GGAGAGCTGC TGGGCCCCGA   1839

GCCACGAACT TGCTGGGTGG TTCTCTGGGC CTCAGTTTCC CTCCTCTGCC AAACGAGGGG   1899

GTCAGCCCAA GATTCTTCAG TCTGGACTAT ATTGGGACTG GGACTTCTGG GTCTCCAGGG   1959

AGGGTATTTA TTGGTCAGGA TGTGGGATTT GAGGAGTGGA GGGGAAAGGG TCCTGCTTTC   2019

TCCTCGTTCT TATTTAATCT CCATTTCTAC TGTGTGATCA GGATGTAATA AGAATTTTA    2079

TTTATTTTCA AAAAAAAAAA AAAAAAAAA AAAAAA                              2116

(2) INFORMATION FOR SEQ ID NO:2:

(i) SEQUENCE CHARACTERISTICS:
        (A) LENGTH: 578 amino acids
        (B) TYPE: amino acid
        (D) TOPOLOGY: linear (ii) MOLECULE TYPE: protein (xi) SEQUENCE DESCRIPTION: SEQ ID NO:2:

Met Arg Gln Gln Asp Ala Pro Lys Pro Thr Pro Ala Ala Arg Arg Cys
1               5                   10                  15

Ser Gly Leu Ala Arg Arg Val Leu Thr Ile Ala Phe Ala Leu Leu Ile
            20                  25                  30

Leu Gly Leu Met Thr Trp Ala Tyr Ala Ala Gly Val Pro Leu Ala Ser
        35                  40                  45

Asp Arg Tyr Gly Leu Leu Ala Phe Gly Leu Tyr Gly Ala Phe Leu Ser
    50                  55                  60

Ala His Leu Val Ala Gln Ser Leu Phe Ala Tyr Leu Glu His Arg Arg
65                  70                  75                  80

Val Ala Ala Ala Ala Arg Gly Pro Leu Asp Ala Ala Thr Ala Arg Ser
                85                  90                  95
```

-continued

```
Val Ala Leu Thr Ile Ser Ala Tyr Gln Glu Asp Pro Ala Tyr Leu Arg
            100                 105                 110
Gln Cys Leu Ala Ser Ala Arg Ala Leu Leu Tyr Pro Arg Ala Arg Leu
        115                 120                 125
Arg Val Leu Met Val Val Asp Gly Asn Arg Ala Glu Asp Leu Tyr Met
    130                 135                 140
Val Asp Met Phe Arg Glu Val Phe Ala Asp Glu Asp Pro Ala Thr Tyr
145                 150                 155                 160
Val Trp Asp Gly Asn Tyr His Gln Pro Trp Glu Pro Ala Ala Ala Gly
                165                 170                 175
Ala Val Gly Ala Gly Ala Tyr Arg Glu Val Glu Ala Glu Asp Pro Gly
            180                 185                 190
Arg Leu Ala Val Glu Ala Leu Val Arg Thr Arg Arg Cys Val Cys Val
        195                 200                 205
Ala Gln Arg Trp Gly Gly Lys Arg Glu Val Met Tyr Thr Ala Phe Lys
    210                 215                 220
Ala Leu Gly Asp Ser Val Asp Tyr Val Gln Val Cys Asp Ser Asp Thr
225                 230                 235                 240
Arg Leu Asp Pro Met Ala Leu Leu Glu Leu Val Arg Val Leu Asp Glu
                245                 250                 255
Asp Pro Arg Val Gly Ala Val Gly Gly Asp Val Arg Ile Leu Asn Pro
            260                 265                 270
Leu Asp Ser Trp Val Ser Phe Leu Ser Ser Leu Arg Tyr Trp Val Ala
        275                 280                 285
Phe Asn Val Glu Arg Ala Cys Gln Ser Tyr Phe His Cys Val Ser Cys
    290                 295                 300
Ile Ser Gly Pro Leu Gly Leu Tyr Arg Asn Asn Leu Leu Gln Gln Phe
305                 310                 315                 320
Leu Glu Ala Trp Tyr Asn Gln Lys Phe Leu Gly Thr His Cys Thr Phe
                325                 330                 335
Gly Asp Asp Arg His Leu Thr Asn Arg Met Leu Ser Met Gly Tyr Ala
            340                 345                 350
Thr Lys Tyr Thr Ser Arg Ser Arg Cys Tyr Ser Glu Thr Pro Ser Ser
        355                 360                 365
Phe Leu Arg Trp Leu Ser Gln Gln Thr Arg Trp Ser Lys Ser Tyr Phe
    370                 375                 380
Arg Glu Trp Leu Tyr Asn Ala Leu Trp Trp His Arg His His Ala Trp
385                 390                 395                 400
Met Thr Tyr Glu Ala Val Val Ser Gly Leu Phe Pro Phe Phe Val Ala
                405                 410                 415
Ala Thr Val Leu Arg Leu Phe Tyr Ala Gly Arg Pro Trp Ala Leu Leu
            420                 425                 430
Trp Val Leu Leu Cys Val Gln Gly Val Ala Leu Ala Lys Ala Ala Phe
        435                 440                 445
Ala Ala Trp Leu Arg Gly Cys Leu Arg Met Val Leu Leu Ser Leu Tyr
    450                 455                 460
Ala Pro Leu Tyr Met Cys Gly Leu Leu Pro Ala Lys Phe Leu Ala Leu
465                 470                 475                 480
Val Thr Met Asn Gln Ser Gly Trp Gly Thr Ser Gly Arg Arg Lys Leu
                485                 490                 495
Ala Ala Asn Tyr Val Pro Leu Leu Pro Leu Ala Leu Trp Ala Leu Leu
            500                 505                 510
```

-continued

```
Leu Leu Gly Gly Leu Val Arg Ser Val Ala His Glu Ala Arg Ala Asp
            515                 520                 525

Trp Ser Gly Pro Ser Arg Ala Ala Glu Ala Tyr His Leu Ala Ala Gly
        530                 535                 540

Ala Gly Ala Tyr Val Gly Tyr Trp Val Ala Met Leu Thr Leu Tyr Trp
545                 550                 555                 560

Val Gly Val Arg Arg Leu Cys Arg Arg Thr Gly Gly Tyr Arg Val
                565                 570                 575

Gln Val
```

(2) INFORMATION FOR SEQ ID NO:3:

(i) SEQUENCE CHARACTERISTICS:
        (A) LENGTH: 587 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Met Lys Glu Lys Ala Ala Glu Thr Met Glu Ile Pro Glu Gly Ile Pro
1                   5                   10                  15

Lys Asp Leu Glu Pro Lys His Pro Thr Leu Trp Arg Ile Ile Tyr Tyr
                20                  25                  30

Ser Phe Gly Val Val Leu Leu Ala Thr Ile Thr Ala Ala Tyr Val Ala
            35                  40                  45

Glu Phe Gln Val Leu Lys His Glu Ala Ile Leu Phe Ser Leu Gly Leu
        50                  55                  60

Tyr Gly Leu Ala Met Leu Leu His Leu Met Met Gln Ser Leu Phe Ala
65                  70                  75                  80

Phe Leu Glu Ile Arg Arg Val Asn Lys Ser Glu Leu Pro Cys Ser Phe
                85                  90                  95

Lys Lys Thr Val Ala Leu Thr Ile Ala Gly Tyr Gln Glu Asn Pro Glu
            100                 105                 110

Tyr Leu Ile Lys Cys Leu Glu Ser Cys Lys Tyr Val Lys Tyr Pro Lys
        115                 120                 125

Asp Lys Leu Lys Ile Ile Leu Val Ile Asp Gly Asn Thr Glu Asp Asp
    130                 135                 140

Ala Tyr Met Met Glu Met Phe Lys Asp Val Phe His Gly Glu Asp Val
145                 150                 155                 160

Gly Thr Tyr Val Trp Lys Gly Asn Tyr His Thr Val Lys Lys Pro Glu
                165                 170                 175

Glu Thr Asn Lys Gly Ser Cys Pro Glu Val Ser Lys Pro Leu Asn Glu
            180                 185                 190

Asp Glu Gly Ile Asn Met Val Glu Glu Leu Val Arg Asn Lys Arg Cys
        195                 200                 205

Val Cys Ile Met Gln Gln Trp Gly Gly Lys Arg Glu Val Met Tyr Thr
    210                 215                 220

Ala Phe Gln Ala Ile Gly Thr Ser Val Asp Tyr Val Gln Val Cys Asp
225                 230                 235                 240

Ser Asp Thr Lys Leu Asp Glu Leu Ala Thr Val Glu Met Val Lys Val
                245                 250                 255

Leu Glu Ser Asn Asp Met Tyr Gly Ala Val Gly Gly Asp Val Arg Ile
            260                 265                 270

Leu Asn Pro Tyr Asp Ser Phe Ile Ser Phe Met Ser Ser Leu Arg Tyr
```

```
                    275                 280                 285
Trp Met Ala Phe Asn Val Glu Arg Ala Cys Gln Ser Tyr Phe Asp Cys
    290                 295                 300

Val Ser Cys Ile Ser Gly Pro Leu Gly Met Tyr Arg Asn Asn Ile Leu
305                 310                 315                 320

Gln Val Phe Leu Glu Ala Trp Tyr Arg Gln Lys Phe Leu Gly Thr Tyr
                325                 330                 335

Cys Thr Leu Gly Asp Asp Arg His Leu Thr Asn Arg Val Leu Ser Met
                340                 345                 350

Gly Tyr Arg Thr Lys Tyr Thr His Lys Ser Arg Ala Phe Ser Glu Thr
                355                 360                 365

Pro Ser Leu Tyr Leu Arg Trp Leu Asn Gln Gln Thr Arg Trp Thr Lys
    370                 375                 380

Ser Tyr Phe Arg Glu Trp Leu Tyr Asn Ala Gln Trp Trp His Lys His
385                 390                 395                 400

His Ile Trp Met Thr Tyr Glu Ser Val Val Ser Phe Ile Phe Pro Phe
                405                 410                 415

Phe Ile Thr Ala Thr Val Ile Arg Leu Ile Tyr Ala Gly Thr Ile Trp
                420                 425                 430

Asn Val Val Trp Leu Leu Leu Cys Ile Gln Ile Met Ser Leu Phe Lys
            435                 440                 445

Ser Ile Tyr Ala Cys Trp Leu Arg Gly Asn Phe Ile Met Leu Leu Met
450                 455                 460

Ser Leu Tyr Ser Met Leu Tyr Met Thr Gly Leu Leu Pro Ser Lys Tyr
465                 470                 475                 480

Phe Ala Leu Leu Thr Leu Asn Lys Thr Gly Trp Gly Thr Gly Arg Lys
                485                 490                 495

Lys Ile Val Gly Asn Tyr Met Pro Ile Leu Pro Leu Ser Ile Trp Ala
                500                 505                 510

Ala Val Leu Cys Gly Gly Val Gly Tyr Ser Ile Tyr Met Asp Cys Gln
            515                 520                 525

Asn Asp Trp Ser Thr Pro Glu Lys Gln Lys Glu Met Tyr His Leu Leu
    530                 535                 540

Tyr Gly Cys Val Gly Tyr Val Met Tyr Trp Val Ile Met Ala Val Met
545                 550                 555                 560

Tyr Trp Val Trp Val Lys Arg Cys Cys Arg Lys Arg Ser Gln Thr Val
                565                 570                 575

Thr Leu Val His Asp Ile Pro Asp Met Cys Val
                580                 585

(2) INFORMATION FOR SEQ ID NO:4:

(i) SEQUENCE CHARACTERISTICS:
        (A) LENGTH: 395 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

Met Tyr Leu Phe Gly Thr Ser Thr Val Gly Ile Tyr Gly Val Ile Leu
1               5                   10                  15

Ile Thr Tyr Leu Val Ile Lys Leu Gly Leu Ser Phe Leu Tyr Glu Pro
                20                  25                  30

Phe Lys Gly Asn Pro His Asp Tyr Lys Val Ala Ala Val Ile Pro Ser
```

-continued

```
           35                 40                  45
Tyr Asn Glu Asp Ala Glu Ser Leu Leu Glu Thr Leu Lys Ser Val Leu
    50                  55                  60

Ala Gln Thr Tyr Pro Leu Ser Glu Ile Tyr Ile Val Asp Asp Gly Ser
65                  70                  75                  80

Ser Asn Thr Asp Ala Ile Gln Leu Ile Glu Glu Tyr Val Asn Arg Glu
                85                  90                  95

Val Asp Ile Cys Arg Asn Val Ile Val His Arg Ser Leu Val Asn Lys
                100                 105                 110

Gly Lys Arg His Ala Gln Ala Trp Ala Phe Glu Arg Ser Asp Ala Asp
                115                 120                 125

Val Phe Leu Thr Val Asp Ser Asp Thr Tyr Ile Tyr Pro Asn Ala Leu
        130                 135                 140

Glu Glu Leu Leu Lys Ser Phe Asn Asp Glu Thr Val Tyr Ala Ala Thr
145                 150                 155                 160

Gly His Leu Asn Ala Arg Asn Arg Gln Thr Asn Leu Leu Thr Arg Leu
                165                 170                 175

Thr Asp Ile Arg Tyr Asp Asn Ala Phe Gly Val Glu Arg Ala Ala Gln
            180                 185                 190

Ser Leu Thr Gly Asn Ile Leu Val Cys Ser Gly Pro Leu Ser Ile Tyr
        195                 200                 205

Arg Arg Glu Val Ile Ile Pro Asn Leu Glu Arg Tyr Lys Asn Gln Thr
    210                 215                 220

Phe Leu Gly Leu Pro Val Ser Ile Gly Asp Asp Arg Cys Leu Thr Asn
225                 230                 235                 240

Tyr Ala Ile Asp Leu Gly Arg Thr Val Tyr Gln Ser Thr Ala Arg Cys
                245                 250                 255

Asp Thr Asp Val Pro Phe Gln Leu Lys Ser Tyr Leu Lys Gln Gln Asn
                260                 265                 270

Arg Trp Asn Lys Ser Phe Phe Arg Glu Ser Ile Ile Ser Val Lys Lys
            275                 280                 285

Ile Leu Ser Asn Pro Ile Val Ala Leu Trp Thr Ile Phe Glu Val Val
        290                 295                 300

Met Phe Met Met Leu Ile Val Ala Ile Gly Asn Leu Leu Phe Asn Gln
305                 310                 315                 320

Ala Ile Gln Leu Asp Leu Ile Lys Leu Phe Ala Phe Leu Ser Ile Ile
                325                 330                 335

Phe Ile Val Ala Leu Cys Arg Asn Val His Tyr Met Val Lys His Pro
                340                 345                 350

Ala Ser Phe Leu Leu Ser Pro Leu Tyr Gly Ile Leu His Leu Phe Val
            355                 360                 365

Leu Gln Pro Leu Lys Leu Tyr Ser Leu Cys Thr Ile Lys Asn Thr Glu
    370                 375                 380

Trp Gly Thr Arg Lys Lys Val Thr Ile Phe Lys
385                 390                 395
```